(12) United States Patent
Jibu

(10) Patent No.: US 8,574,925 B2
(45) Date of Patent: Nov. 5, 2013

(54) FLUORESCENCE ANALYSIS METHOD USING FLUORESCENT-ACTIVATING ANTIBODIES

(75) Inventor: Masaki Jibu, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 1430 days.

(21) Appl. No.: 11/083,084

(22) Filed: Mar. 18, 2005

(65) Prior Publication Data

US 2005/0221387 A1 Oct. 6, 2005

Related U.S. Application Data

(63) Continuation-in-part of application No. PCT/JP03/11926, filed on Sep. 18, 2003.

(30) Foreign Application Priority Data

Sep. 19, 2002 (JP) .................. P2002-273833

(51) Int. Cl.
G01N 33/542 (2006.01)
G01N 33/533 (2006.01)
G01N 33/53 (2006.01)

(52) U.S. Cl.
USPC ............. 436/537; 436/546; 436/172; 435/7.1

(58) Field of Classification Search
None
See application file for complete search history.

(56) References Cited

U.S. PATENT DOCUMENTS

| 6,437,099 B1 | 8/2002 | Jibu | |
|---|---|---|---|
| 2003/0065150 A1 | 4/2003 | Jibu | ............... 530/388.1 |

FOREIGN PATENT DOCUMENTS

| JP | 03-048765 A | 3/1991 |
|---|---|---|
| JP | 04-211363 A | 8/1992 |
| JP | 09-005324 A | 1/1997 |
| JP | 11-183477 A | 7/1999 |

OTHER PUBLICATIONS

Machine translation of JP 11-183477, obtained from http://dossier1.ipdl.inpit.go.jp on Nov. 6, 2007.*
Harlow, E. and Lane, D., Antibodies: A Laboratory Manual (1988) Cold Spring Harbor Laboratory Press, Cold Spring Harbor, NY, pp. 23-26.*
Greenspan et al. "Defining epitopes: It's not as easy as it seems" Nature Biotechnology vol. 17 (Oct. 199), pp. 936-937.*

(Continued)

*Primary Examiner* — Christine Foster
(74) *Attorney, Agent, or Firm* — Drinker Biddle & Reath LLP

(57) ABSTRACT

An object of this invention is to provide a fluorescence analysis method that enables analysis (including imaging) of in vivo substances, etc., using antigen-antibody reactions to be carried out simply, at high sensitivity, and yet continuously and in real time. This invention's fluorescence analysis method comprises: a mixing step of obtaining a mixed solution of a sample solution and an antibody-dye solution, the sample solution containing an analyte, the antibody-dye solution containing an antibody and a dye at predetermined concentrations respectively, the antibody having an antigen-binding site a part of which recognizes the dye and a remaining part of which recognizes the analyte, the dye being recognized by the antibody and changing from being non-fluorescent to fluorescent upon binding with the antibody; a measurement step of illuminating the mixed solution with excitation light and obtaining a measurement value by measuring an intensity of fluorescence emitted from the mixed solution; and a computation step of determining a concentration of the analyte from the measurement value based on a predetermined relationship between fluorescence intensity and analyte concentration.

11 Claims, 12 Drawing Sheets

(56) References Cited

OTHER PUBLICATIONS

Academic Press Dictionary of Science and Technology, definition for the term "polyclonal"; Oxford: Elsevier Science & Technology (1996); retrieved Oct. 22, 2008, from http://www.credoreference.com/entry/3144515/.*
Janeway et al. Immunobiology: the Immune System in Health and Disease (1999), Elsevier Science Ltd/Garland Publishing, New York, NY, Fourth Edition, pp. 34-35.*
Lederman et al. "A single amino acid substitution in a common African allele of the CD4 molecule ablates binding of the monoclonal antibody, OKT4" Mol Immunol. Nov. 1991;28(11):1171-81.*
Colman et al. Research in Immunology, 1994; 145(1): 33-36.*
"Fluoroimmunoassay", Kiyoshi Miyai Kodansha Scientific, 1985, p. 57-58.
Kiyoshi Ichihara, et al., "Kinetic Aspects of the Antigen-Antibody Reaction in Various Radioimmuno Assays: Effect of Delayed Addition of Labeled or Unlabeled Antigens of Sensitivity of Assay", Clinica Chimica Acta, vol. 98, 1979, p. 87-101.
Tomomichi Iwaki, et al., "Antibodies for Fluorescent Molecular Rotors", BioChemistry, 32, 1993, p. 7589-7592.
Masahiko Onodera Kyoritsu Shuppan, "Principles of Fluorescence Measurement and Application to Biological Systems", 1974, p. 189-197.
"Introduction to Immonassay", Nanzando, 1987, p. 70, Edwards, R. Akira Kawaoi,"Illustrated Technology of Immunofluorescence", 1983, p. 134-139, Soft Science, Inc. Tokyo.

"New Biochemistry Experiment Course," vol. 12, 1$^{st}$ Edition, 1$^{st}$ Impression, Molecular Immunology III—Antigen, Antibody and Complement, The Japanese Biochemical Society, ed. (Feb. 5, 1992) (partial English-language translation: p. 1, line 7, to p. 2, line 15).
"Biochemistry Experiment Method," vol. 10, 1$^{st}$ Edition, 1$^{st}$ Impression, Monoclonal Antibody (Oct. 20, 1989) (partial English-language translation supervised by T. Osawa: p. 91, lines 10-16).
Kung et al., "Fluorescent Molecular Rotors: A New Class of Probes for Tublin Structure and Assembly," *Biochemistry*, vol. 28, pp. 6678-6686, 1989.
Loutfy, "High-Conversion Polymerization Fluorescence Probes. 1. Polymerization of Methyl Methacrylate," *Macromolecules*, vol. 14, pp. 270-275, 1981.
Law et al., Spectroscopy of Dyes in Polymer Matrices: Dual Fluorescence of a [p-(Dialkylamino)benzylidene]malononitrile Dye in Poly-(vinyl acetate) Matrices,*Macromolecules*, vol. 14, pp. 587-591, 1981.
Koike et al., "Specificity of mouse hybridoma antibodies to DNA. II. Phospholipid reactivity and biological false positive serological test for syphilis," *Clin. Exp. Immunol.* (1984) vol. 57, pp. 345-350.
Fouraux et al., "Cross-reactivity of the anti-La monoclonal antibody SW5 with early endosome antigen 2," *Immunology* (2002), vol. 106, pp. 336-342.
Alberts et al., "Molecular Biology of the Cell," Third Edition, Garland Publishing Inc. (1994) pp. 1239-1244.
Faaber et al., "Cross-reactivity of anti-DNA antibodies with proteoglycans," *Clin. Exp. Immunol.* (1984) vol. 55, pp. 502-508.

\* cited by examiner

FLUORESCENCE ANALYSIS METHOD USING FLUORESCENT-ACTIVATING ANTIBODIES

RELATED APPLICATIONS

This application is a continuation-in-part of the International Patent Applications No. PCT/JP03/11926, filed Sep. 18, 2003.

BACKGROUND OF THE INVENTION

1. Field of the Invention

This invention concerns a fluorescence analysis method that uses a dye that changes from being non-fluorescent to fluorescent upon binding with an antibody.

2. Related Background Art of the Invention

The analysis of biological components and various chemical substances (medical drugs, environmental pollutants, etc.) in a living body is extremely important for academic research and the diagnosis and treatment of illnesses. However, since generally-used prior-art methods for analyzing these substances require the sampling of body fluid, extraction of tissue, and complex, time-consuming preprocesses for removing foreign substances, the development of analysis methods that enable in vivo substances, etc., to be analyzed simply and yet at high sensitivity were desired.

Immunoassay (immunoassay and immunometric assay) methods using fluorescent dye labeled antibodies have thus been developed as one of the methods enabling such analysis. By such an immunoassay method, analysis of high selectivity is enabled by a specific molecule recognition function based on an antigen-antibody reaction and selective measurement of the analyte is enabled by fluorescence analysis without removing foreign substances. An antibody, which has been labeled in advance by a fluorescent dye, is generally used as the fluorescent dye labeled antibody, and a single substance (antigen) is recognized specifically by an antigen-binding site. In Japanese Laid-Open Patent Application No. 4-211363 is disclosed a bispecific hybrid monoclonal antibody having two antigen-binding sites, one of which is induced by a tissue plasminogen activator and the other of which is induced by a fluorescent substance or other label. In Japanese Laid-Open Patent Application No. 9-5324 is disclosed an antibody for an antigen formed by adding a non-fluorescent dye to an immunity substance. Furthermore, in Japanese Laid-Open Patent Application No. 11-183477 is disclosed a fluorescence immunoassay method, with which a fluorescence intensity change is measured under the presence of insulin, based on an antigen-antibody reaction between a covalently bound substance (MG-labeled insulin) of insulin and malachite green (MG) and an anti-MG-Ins antibody, for which this covalently bound substance is an antigen.

SUMMARY OF THE INVENTION

That an antigen-antibody reaction is irreversible is a common knowledge among those skilled in the art (see, for example, "Fluoroimmunoassay," Kiyoshi Miyai et al., Kodansha Scientific, p. 57-58 (1985); K. Ichihara et al., Clinica Chimica Acta vol. 98, p. 87-100 (1979); etc.). The present inventor has found that with prior-art immunoassay methods, it is thus difficult to perform in real time continuous analysis of the variation of the amounts of in vivo substances, etc.

The present inventor has also found that, in the antigen-antibody reaction of the MG-labeled insulin and the anti-MG-Ins antibody, described in Japanese Laid-Open Patent Application No. 11-183477, a competition reaction occurs between insulin and the MG-labeled insulin at a site that recognizes insulin (insulin-recognizing site), a steady state, in which nearly all of the MG-labeled insulin occupy the insulin-recognizing sites, is achieved in the final stage, that is, the competition reaction between insulin and MG-labeled insulin is an irreversible reaction, and it is thus difficult to perform in real time, continuous analysis of the variation of the amounts of in vivo substances, etc., with the immunoassay method using this antigen-antibody reaction.

This invention has been made in view of the above issues of the prior arts. An object of this invention is to provide a fluorescence analysis method that enables analysis (including imaging) of in vivo substances, etc., using antigen-antibody reactions to be carried out simply, at high sensitivity, and yet continuously and in real time.

As a result of continuing diligent research towards achieving the above object, the present inventor has found that antigen-antibody reactions, wherein an antibody, invented by the present inventor and already being applied for a patent as described in Japanese Laid-Open Patent Application No. 9-5324, that is, an antibody for an antigen, formed by adding a non-fluorescent dye to an immunity substance, is used under the presence of the non-fluorescent dye in singular form and the immunity substance in singular form, are surprisingly reversible and that by performing fluorescence analysis using these reversible antigen-antibody reactions, the above object can be achieved and has thus arrived at the present invention.

This invention provides a fluorescence analysis method comprising: a mixing step of obtaining a mixed solution of a sample solution and an antibody-dye solution, the sample solution containing an analyte, the antibody-dye solution containing an antibody and a dye at predetermined concentrations respectively, the antibody having an antigen-binding site a part of which recognizes the dye and a remaining part of which recognizes the analyte, the dye being recognized by the antibody and changing from being non-fluorescent to fluorescent upon binding with the antibody; a measurement step of illuminating the mixed solution with excitation light and obtaining a measurement value by measuring an intensity of fluorescence emitted from the mixed solution; and a computation step of determining a concentration of the analyte from the measurement value based on a predetermined relationship between fluorescence intensity and analyte concentration.

With this invention's fluorescence analysis method, in the mixed solution of the above-mentioned antibody-dye solution and the above-mentioned sample solution, the above-mentioned dye and the above-mentioned analyte respectively bind with the above-mentioned antibody through antigen-antibody reactions, and the dye that binds with the antibody changes from being non-fluorescent to fluorescent. In this process, since the binding of the dye to the antibody is influenced by the amount of the coexisting analyte, the intensity of the fluorescence that is emitted from the dye that has become bound to the antibody is inhibited or enhanced in accordance with the amount of the coexisting analyte. Thus in a solution in which the amounts of the dye and the antibody are fixed, fluorescence intensity and analyte concentration are correlated and, based on such a correlation (a calibration curve), the analyte concentration is determined from the actual measurement value of the fluorescence intensity. Thus with this invention's fluorescence analysis method, a highly sensitive analysis of high selectivity is enabled by the specific molecule recognition function provided by the antigen-antibody reactions, and by fluorescence analysis, which is not readily affected by foreign substances, the analyte can be measured selectively in a simple manner without removing the foreign substances. Since the antigen-antibody reactions of this invention, that is, the binding reaction of the portion of the above-mentioned antibody that recognizes the above-mentioned dye with the above-mentioned dye and the binding reaction of the portion of the above-mentioned antibody that recognizes the above-mentioned analyte with the above-mentioned analyte are reversible in contrast to the common knowledge of the prior art that antigen-antibody reactions are irreversible and the portions of the above-mentioned antibody that recognize the above-mentioned dye and the above-mentioned analyte will thus not become occupied by the above-mentioned dye or above-mentioned analyte and reach a steady state, the variation of the fluorescence intensity in accordance with the variation of the analyte amount can be made use of to enable continuous analysis (including imaging) in real time.

This invention's fluorescence analysis method may thus furthermore comprise: a continuous analysis step of adding and mixing more sample solution into the mixed solution subsequent to the computation step and then executing the measurement step and the computation step to repeatedly determine analyte concentrations. By including such a continuous analysis step, continuous analysis of the analyte concentration in real time is enabled.

The above-mentioned computation step preferably comprises the steps of: obtaining a corrected fluorescence intensity value by correcting the measurement value in accordance with volume change that accompanies an addition of the sample solution; determining an analyte concentration in the mixed solution from the corrected fluorescence intensity value based on a predetermined relationship between corrected fluorescence intensity values and analyte concentration in the mixed solution; and determining an analyte concentration in the sample solution from the analyte concentration in the mixed solution. By including these steps, even in a case where the concentration changes of the dye and the antibody in the mixed solution that accompany the addition of the sample solution cannot be ignored, correction to the state without such concentration changes can be performed to adequately prevent the lowering of the precision of analysis.

This invention's fluorescence analysis method may further comprise: a mixing step of obtaining a mixed solution of a standard solution and an antibody-dye solution, the standard solution containing an analyte at a predetermined concentration, the antibody-dye solution containing an antibody and a dye at predetermined concentrations respectively, the antibody having an antigen-binding site a part of which recognizes the dye and a remaining part of which recognizes the analyte, the dye being recognized by the antibody and changing from being non-fluorescent to fluorescent upon binding with the antibody; a measurement step of illuminating the mixed solution with excitation light and obtaining a measurement value by measuring an intensity of fluorescence emitted from the mixed solution; a continuous measurement step of adding and mixing more standard solution into the mixed solution and thereafter executing the measurement step to repeatedly determine measurement values of fluorescence intensity; and a calibration curve preparation step of determining a relationship between fluorescence intensity and analyte concentration based on added amounts of the analyte and the measurement values obtained in the measurement step and the continuous measurement step. By including these steps, a correlation between fluorescence intensity and analyte concentration, that is, a calibration curve can be obtained efficiently.

The above-mentioned calibration curve preparation step preferably comprises the steps of: obtaining a corrected fluorescence intensity value by correcting the measurement value in accordance with volume change that accompanies an addition of the standard solution; computing an analyte concentration in the mixed solution; and determining a relationship between the corrected fluorescence intensity value and the analyte concentration in the mixed solution. By including these steps, even in a case where the concentration changes of the dye and the antibody in the mixed solution that accompany the addition of the sample solution cannot be ignored, correction to the state without such concentration changes can be performed to adequately prevent the lowering of the precision of analysis.

As the above-mentioned dye of this invention, a dye having a triphenylmethane structure or a dye having a diphenylmethane structure is preferable and malachite green or auramine O is more preferable.

As the above-mentioned antibody of this invention, (i) an antibody, for which a covalently bound substance of the above-mentioned dye and the above-mentioned analyte is an antigen, or (ii) an antibody, for which a covalently bound substance of the above-mentioned analyte and a dye, recognized by the antibody and having, in common with the dye, a structure necessary for the change from being non-fluorescent to fluorescent upon binding with the above-mentioned antibody is an antigen, is preferable. As a combination of such an antibody and a dye, (i) a combination, wherein the above-mentioned antibody is an antibody, for which a covalently bound substance of malachite green and the above-mentioned analyte is an antigen, and the above-mentioned dye is malachite green, or (ii) a combination, wherein the above-mentioned antibody is an antibody, for which a covalently bound substance of malachite green and the above-mentioned analyte is an antigen, and the above-mentioned dye is auramine O, is more preferable.

Furthermore, the above-mentioned analyte of this invention's fluorescence analysis method is preferably selected from the group consisting of proteins, hormones, vitamins, bacterial cells, environmental pollutants, and medical drugs that are to be subject to immunoassay.

DESCRIPTION OF THE PREFERRED EMBODIMENTS

Figure 1:
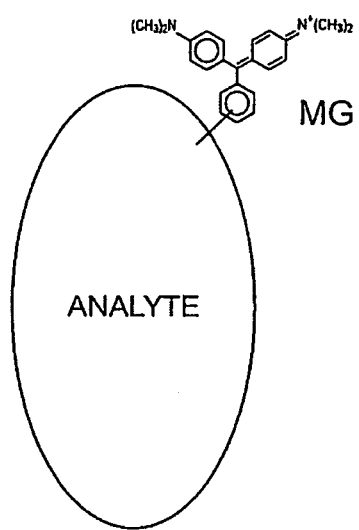
FIG. 1 is a schematic view illustrating an MG-analyte complex that is an antigen.

A preferred embodiment of this invention's fluorescence analysis method shall now be described in detail with reference to the drawings. In the drawings, parts that are the same or equivalent shall be provided with the same symbols.

(Dye)

A dye used in this invention is not restricted in particular as long as it is non-fluorescent in water or other normal solvent and changes to being fluorescent upon binding with an antibody to be described later. With this invention, non-fluorescent means that a substance is practically not fluorescent, and preferably under normal measurement conditions, a fluorescence spectrum is not exhibited or only extremely weak fluorescence is exhibited. It is deemed that fluorescence analysis (fluorescence spectral analysis) by a commercially available apparatus, etc., is practically impossible (Yasuharu Nishikawa, et al., "Fluorescence and Phosphorescence Analysis Methods," Kyoritsu Shuppan, p. 30, 1984). As such a dye that practically does not exhibit fluorescence, one with which a fluorescence quantum yield is less than 1% under specific conditions is preferable and one with which the fluorescence quantum yield is no more than 0.01% under specific conditions is more preferable.

With this invention, that a dye changes from being non-fluorescent to fluorescent upon binding with an antibody means that the dye, which is practically not fluorescent, becomes fluorescent (increases in fluorescence) when it becomes bound with an antibody and that fluorescence analysis is enabled by thus obtaining an analytical sensitivity greater than or equal to the sensitivity obtained in normal fluorescence analysis. Preferably, the dye changes from a state wherein the fluorescence quantum yield is extremely small under normal measurement conditions (for example, no more than 0.01%) to a state of high fluorescence quantum yield (for example, no less than 1%) by binding (interacting) with the antibody by the process of this invention.

Here, in regard to the increase of the fluorescence intensity when the dye changes from being non-fluorescent to fluorescent, the fluorescence quantum yield preferably increases by at least 10 times or more, more preferably increases by at least 100 times or more, and especially preferably increases by at least 1000 times or more.

The dye that can be used in this invention does not necessarily need to exhibit absorption in the visible range (exhibit an absorption maximum at 350 nm or more) and may exhibit absorption in the ultraviolet range (exhibit an absorption maximum at 350 nm or less) or may have an absorption band extending into the visible range.

The molecular structure of the dye that can be used in this invention is not restricted in particular. Various chromophores can be selected as a chromophore of a dye. A dye containing a chromophore that is stable in the vicinity of neutral pH is preferably used.

As such a dye, for example, a dye having a triphenylmethane skeleton in the molecular structure (see for example, Kodansha Scientific Co., Ltd., Makoto Okawara, ed., "Organic Colorants—A Handbook of Data of Selected Dyes for Electro-Optical Applications") is preferable, and as such a triphenylmethane-based dye, malachite green (MG), which has the following chemical structure, is especially preferable.

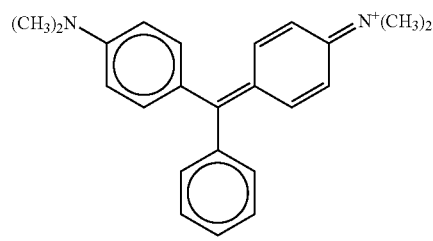

Also as such a dye, a dye having a diphenylmethane skeleton in the molecular structure (see for example, Kodansha Scientific Co., Ltd., Makoto Okawara, ed., "Organic Colorants—A Handbook of Data of Selected Dyes for Electro-Optical Applications") is preferable, and as such a diphenylmethane-based dye, auramine O (AO), which has the following chemical structure, is especially preferable.

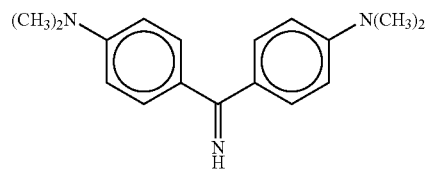

When a dye such as malachite green or auramine O is used, an increase of the fluorescence quantum yield of approximately 1000 times or more can be obtained. Besides these dyes, CVJ (9-(dicyanovinyl) julolidine) based dyes, ANS (anilinonaphthalene) based dyes, TNS (p-toluidinylnaphthalene) based dyes, and DNP (2,4-dinitrophenyl) based dyes may also be used favorably.

Though malachite green is substantially non-fluorescent in an aqueous solution, it becomes fluorescent upon binding with an anti-MG antibody. The present inventor presumes this to be due to the restraining of the intramolecular motion of malachite green by the antibody such that after absorption of excitation light by malachite green, the probability of return to the ground state by the thermal processes (non-radiative processes) based on intramolecular motion is decreased relatively and the probability of deactivation by the radiative process (emitting fluorescence) is thus increased relatively, with respect to the state of being in an aqueous solution. This applies in general to dyes having similar chemical structures and exhibiting similar deactivation processes (diphenylmethane-based dyes and triphenylmethane-based dyes). Though differing in mechanism, other dyes are also known wherein fluorescence intensity of the dyes increases significantly by antibodies (Tomomichi Iwaki et al., Biochemistry 1993, Vol. 32, p. 7589-7592; Protein, Nucleic Acids, and Enzymes Supplement "Principles of Fluorescence Measurement and Application to Biological Systems," Masahiko Onodera (Yuichi Kanaoka, et al., ed.) Kyoritsu Shuppan, 1974, p. 189-197).

(Analyte)

The analyte to which this invention's fluorescence analysis method can be applied is not restricted in particular as long as the substance binding with the above-described dye (complex) functions as an antigen. The analyte in itself concerning this invention does not necessarily have to be an immunity substance. Though an antibody is normally not obtained for a tolerogenic substance or low antigenic substance, with the present invention, since an antibody is obtained for which a complex, resulting from the binding of the analyte with the dye that is an artificial compound, is used as an antigen, and since even if the analyte itself is a tolerogenic substance or low antigenic substance, there is a high possibility that the complex with the dye is an immunity substance, an antibody can be obtained by the method to be described later.

Thus with this invention's fluorescence analysis method, a wide range of substances, excluding inorganic ions and organic ions are applicable as the analyte. Among such substances, that which is selected from the group consisting of proteins (insulin, etc.), hormones, vitamins, bacterial cells, environmental pollutants, and medical drugs that are to be subject to immunoassay is preferable as the analyte.

The after-described antibody can be prepared for all analytes for which the analyte itself has a molecular weight (normally, no less than approximately 5000) adequate for it to be an antigen. Thus even if the analyte is a tolerogenic substance for an animal to be immunized (for example, when the analyte is an in vivo component for that animal species), it is possible to prepare the after-described antibody. This is because the antigen concerning this invention is not the analyte itself but is an artificial substance in which the dye that is an artificial substance is bridged to the analyte.

Even in a case where the analyte itself does not have an adequate molecular weight for it to be an antigen, a substance, with which a carrier that exhibits antigenicity is additionally bound covalently and bridged to a complex of the dye and the analyte, may be prepared and used as an antigen. Even in this case, a following antibody, with which the antigen-recognizing site has forms that recognize both the dye and the analyte, is obtained.

(Antibody)

With the antibody used in this invention, a part of an antigen-binding site thereof recognizes the dye and a remaining part of the antigen-binding site recognizes the analyte. That is, with the antibody concerning this invention, a single antigen-binding site is spatially divided into a plurality of parts and a part thereof recognizes the dye and a remaining part recognizes the analyte. An art with which a single antigen-binding site is made to have a plurality of different functions has not existed priorly and has been found for the first time by the present inventor.

Such an antibody concerning this invention is preferably formed so that a covalently bound substance of the dye and the analyte used in this invention's fluorescence analysis method is an antigen. For example, in the case where the dye used for analysis is malachite green, the above-mentioned antibody is preferably an antibody with which a covalently bound substance of malachite green and the analyte is an antigen.

The dye used for analysis and the dye for obtaining the antibody do not necessarily have to be the same. Dyes, which are having in common the structure necessary for being recognized by the antibody and changing from being non-fluorescent to fluorescent upon binding with the antibody, may be used. The combination of malachite green and auramine O can be cited as an example of a combination of dyes having such a structure in common. Thus for example, when the dye used for analysis is auramine O, the above-mentioned antibody may be an antibody for which a covalently bound substance of malachite green and the analyte is an antigen.

(Preparation of the Complex (Antigen) of the Dye and the Analyte)

The method of preparing the complex (antigen) of the dye and the analyte concerning this invention is not restricted in particular. For example, the above-described analyte and the dye having at least one appropriate functional group may be mixed by stirring for a predetermined amount of time and the fraction of the antigen that is the complex of the dye and the analyte may be separated using gel permeation chromatography.

Furthermore, if necessary, the obtained antigen may be purified using a purification means that applies, for example, an inmunoreaction (Koichiro Kawashima (trans.) "Introduction to Immunoassay," Nanzando, p. 70, 1987). The concentration of the antigen obtained can be quantified, for example, by the Lowry method.

(Preparation of Antiserum)

The above-described antibody concerning this invention can be prepared favorably by the immunity process described later.

The above-described antibody concerning this invention can be prepared by administering the above-described complex (antigen) to an immune animal and thereafter sampling blood from the immune animal and separating antiserum from this blood. The immune animal to which the above-described complex (antigen) is administered is not restricted in particular. Rabbits, guinea pigs, etc., can be used favorably. The immune adjuvant that can be used is not restricted in particular. A generally-used incomplete Freund's adjuvant, aluminum adjuvant, etc., can be used favorably. Furthermore, the immunization injection method that can be used is not restricted in particular. For example, in the case of a guinea pig, subcutaneous injection, intraperitoneal injection, etc., can be used favorably. In regard to the confirmation of production and sampling of the antiserum, these can be carried out by performing booster if necessary and then carrying out test sampling and examination of the antibody titer.

The method of separating the sampled antiserum is not restricted in particular. A generally-used method, for example, the method of congealing the sampled blood and thereafter separating the serum by centrifugation, may be used. The specific antibody activity of the obtained antiserum against the above-mentioned complex (antigen) can be measured favorably by an enzymatic immunoreaction, etc. ("Illustrated Fluorescence Antibody Method—Principals, Techniques, and Applications—"Akira Kawaoi, p. 135-138, Soft Science Inc. (1983)).

(Preparation of IgG Fraction)

With this invention, the antibody in the above-described antiserum may be used. An IgG fraction, obtained by purification of the antiserum may be used as the antibody instead. The method of purifying such an IgG fraction from the antiserum is not restricted in particular. Salting out, gel filtration technique, ion exchange chromatography, etc., can be used favorably and the protein A method can be used especially favorably. The IgG fraction obtained may be concentrated further by centrifugation, and a concentration of the IgG fraction may thereby be adjusted to a predetennined concentration.

(Preparation of Antigen-Binding Fragment (Fab))

With this invention, it is more preferable to use an antigen-binding fragment (Fab), prepared from the above-described IgG fraction, as the antibody. When an antigen-binding fragment (Fab) is used, precipitation of the immunocomplex, formed with the analyte, tends to be prevented more definitely. Such a method of preparing an antigen-binding fragment (Fab) from the IgG fraction is not restricted in particular. For example, the antigen-binding fragment (Fab) can be obtained by digesting the IgG fraction using a digestive enzyme (a digestive enzyme, papain, etc.). Preferably the obtained antigen-binding fragment (Fab) is purified by an immunoprecipitation method, such as a protein A method, etc., and may furthermore be concentrated by centrifugation. Thus, a concentration of the antigen-binding fragment (Fab) may be adjusted to a predetermined concentration.

(Principles of this Invention's Fluorescence Analysis Method)

With this invention's fluorescence analysis method, when the above-described antibody, the above-described dye, and the above-described analyte are mixed in a solution, the dye and the analyte bind respectively to the antibody through antigen-antibody reactions, and the dye that has become bound to the antibody changes from being non-fluorescent to fluorescent. In this process, the binding of the dye to the antibody is influenced by the amount of the coexisting analyte and the intensity of the fluorescence emitted from the dye bound to the antibody is inhibited or enhanced according to the amount of the coexisting analyte. In contrast to the common knowledge of the prior art that an antigen-antibody reaction is irreversible, this invention's antigen-antibody reactions are reversible and the fluorescence intensity varies in accordance with the variation of the amount of the analyte. The present inventor assumes the principles of this invention's fluorescence analysis method to be as follows. Here, a description shall be provided for an exemplary case of using malachite green (referred to hereinafter as "MG") as a representative of a dye used in this invention.

Figure 2:
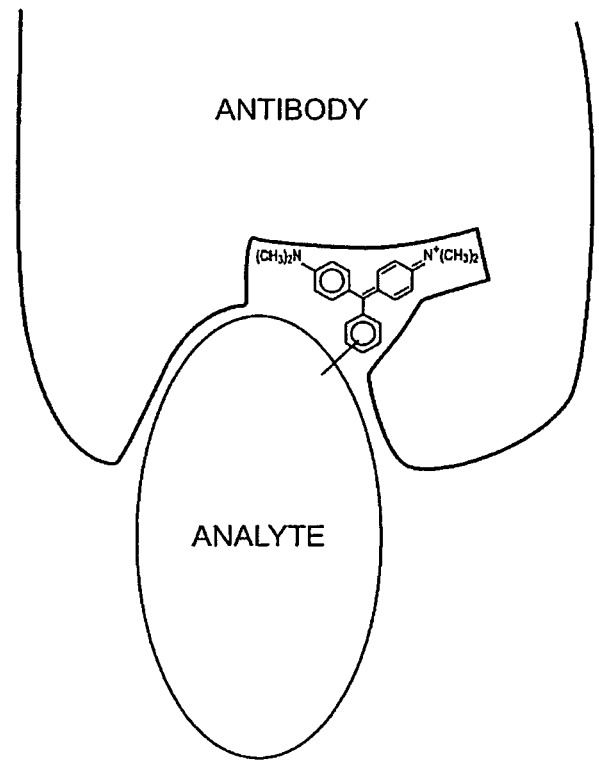
FIG. 2 is a schematic view illustrating a state in which an antigen-recognizing site has recognized both MG and an analyte.

Since the molecular weight of MG is too small to act alone as an antigen, in order to obtain an anti-MG antibody, a compound, in which MG is bridged by a covalent bond to a substance (carrier) of large molecular weight, is administered as an antigen to an animal. In this case, if the analyte is selected as the carrier, the antigen will be a covalent bond complex of MG and the analyte (an MG-analyte complex, such as that shown in FIG. 1). Antibodies (IgG, etc.) that are thus obtained include those with which the antigen-recognizing site has a form that recognizes both MG and the analyte as illustrated in FIG. 2.

Figure 3:
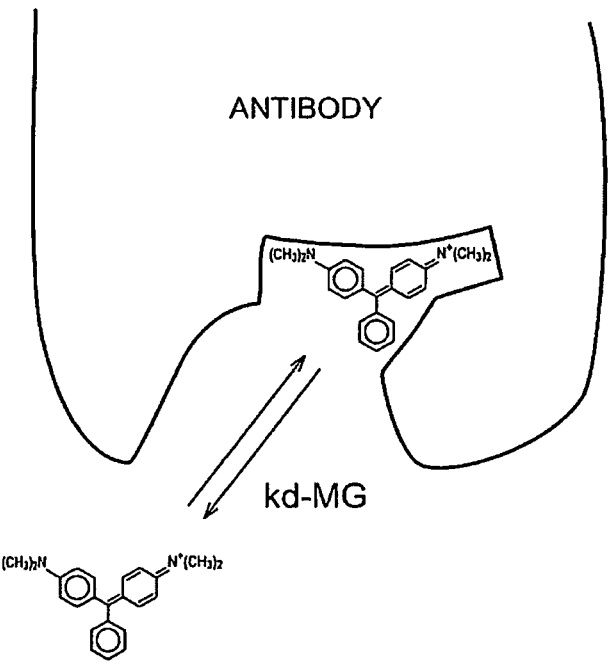
FIG. 3 is a schematic view illustrating an antigen-antibody reaction of MG and an antibody.
Figure 4:
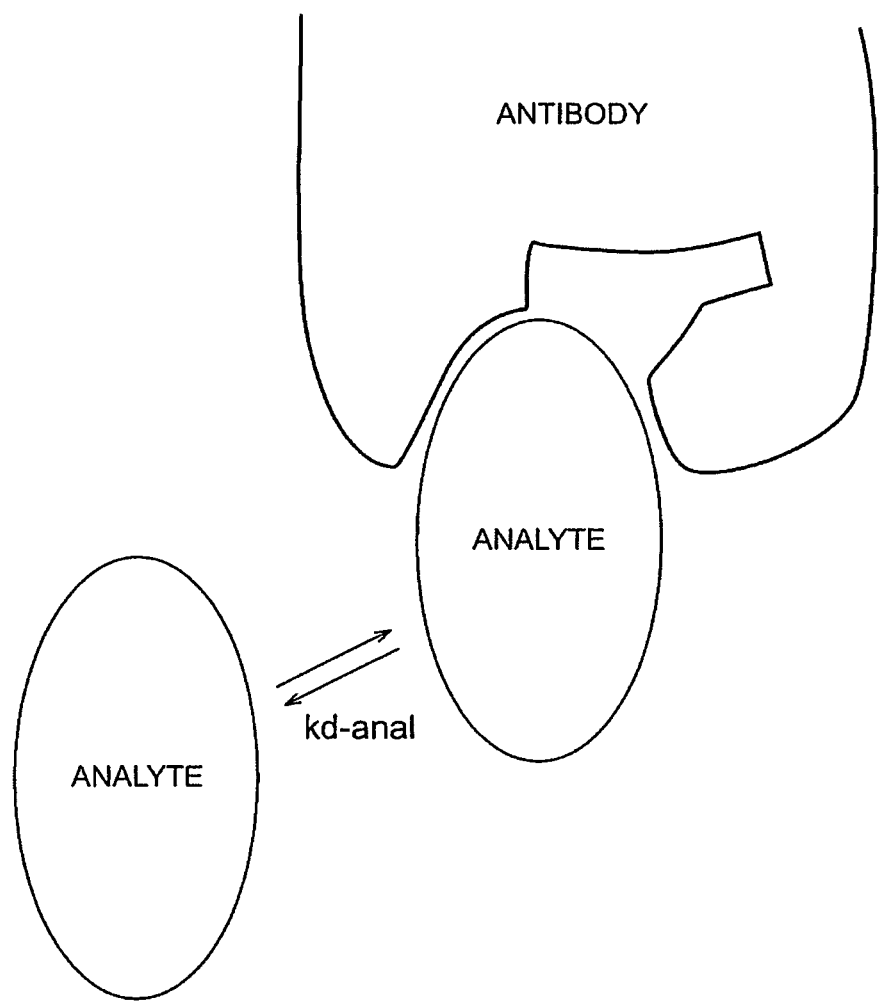
FIG. 4 is a schematic view illustrating an antigen-antibody reaction of an analyte and an antibody.

When this antibody and MG are mixed in a solution, an antigen-antibody reaction occurs, and MG becomes bound (non-covalently) to the antigen-binding site of the antibody as illustrated in FIG. 3. Here, let kd-MG be the dissociation rate constant for this bond. Meanwhile, when the analyte is mixed with this antibody in a solution, the analyte likewise becomes bound (non-covalently) to the antigen-binding site of the antibody as shown in FIG. 4. Here, let kd-anal be the dissociation rate constant for this bond. However, since MG and the analyte are both only portions of the antigen (that is, the MG-analyte complex), the binding of MG alone to the antibody (referred to hereinafter as the "MG-antibody bond") and the binding of the analyte alone to the antibody (referred to hereinafter as the "analyte-antibody bond") are presumed to be respectively weaker than the binding of the MG-analyte complex, which is the original antigen, to the antibody. Thus if kd-Ag is the dissociation rate constant of the biding of the MG-analyte complex to the antibody, since the lower the dissociation rate constant, the less likely dissociation will occur, that is, the stronger the bond, the relationships among the respective dissociation rate constants will be:

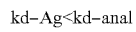

Figure 5:
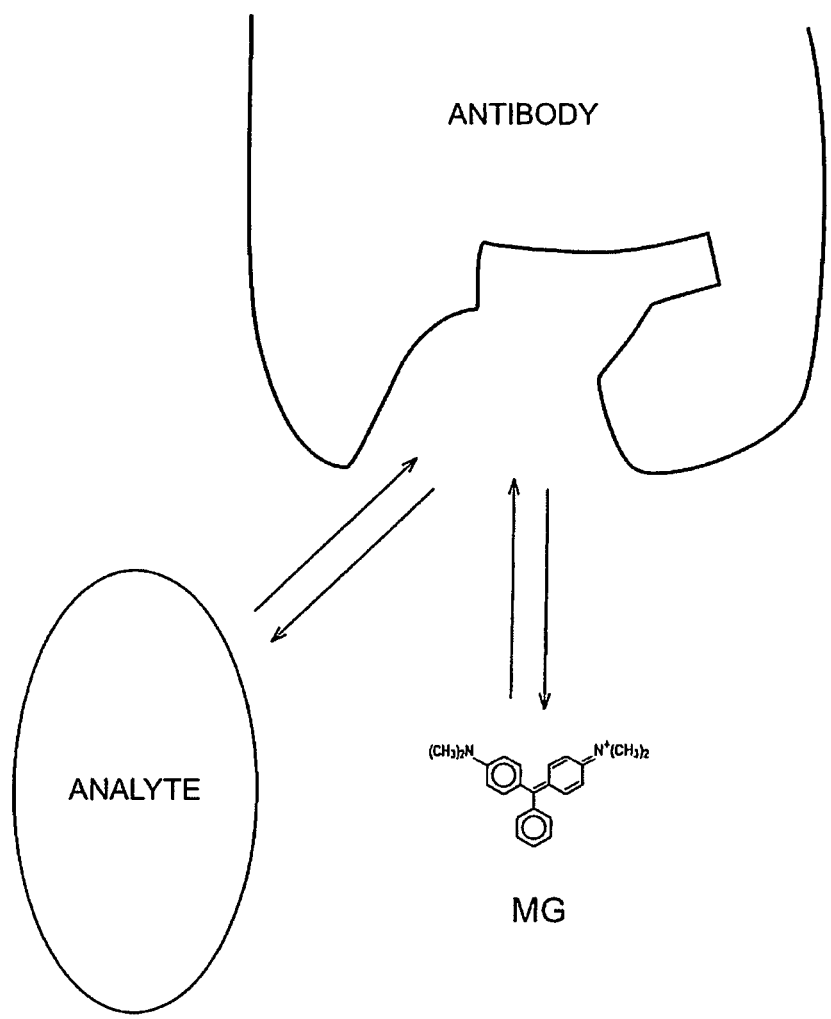
FIG. 5 is a schematic view illustrating antigen-antibody reactions of three components of an antibody, MG, and an analyte.
Figure 6A:
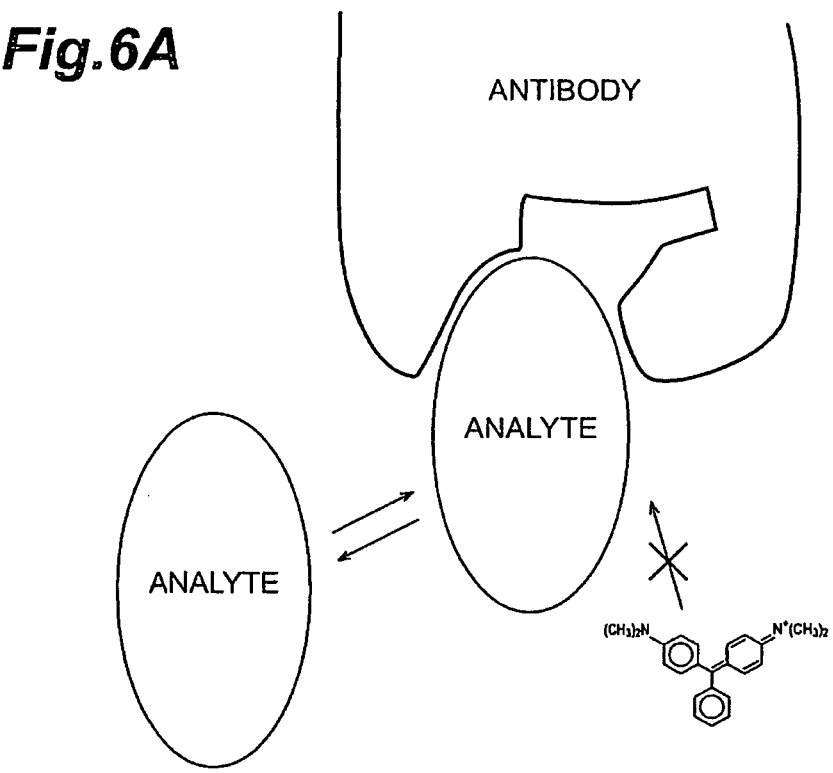
FIG. 6A and FIG. 6B are respectively schematic views illustrating an influence of an analyte on an antigen-antibody reaction between an antibody and MG.
Figure 6B:
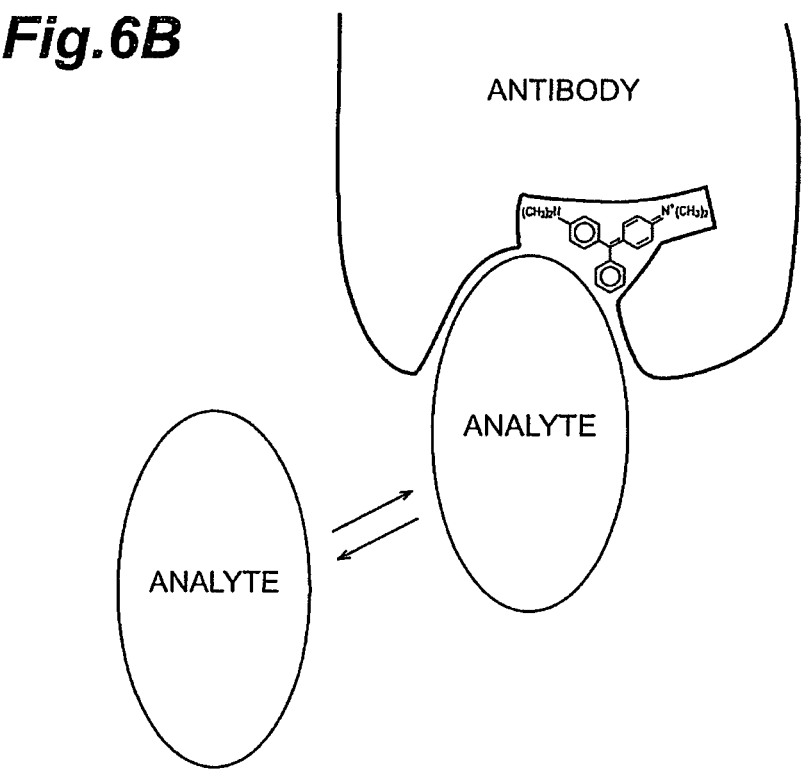

Next, if the three components of the antibody, MG, and analyte are mixed, both MG and the analyte will bind to the antigen-binding site of the antibody as shown in FIG. 5. It is presumed that the state in which both MG and the analyte are fitted to the antigen-binding site is the most stable since the state is close to the state shown in FIG. 2 in which the MG-analyte complex is bound to the antibody. However, there is the possibility that the analyte will influence the MG-antibody bond in this state and there is also the possibility that MG will influence the analyte-antibody bond in this state. It is assumed that the reaction kinetics are determined by the respective dissociation rate constants and the respective positions in the antigen-binding site that are occupied by MG and the analyte (which of MG and the analyte are positioned deeper inside). For example, if MG is bound to a deeper position than the analyte, the binding of MG will be inhibited as shown in FIG. 6A when the analyte becomes bound to the antibody ahead, while when MG is bound ahead, the binding of MG will be made more stable and enhanced by the subsequent binding of the analyte as shown in FIG. 6B in comparison to the case of MG alone. Such enhancement is equivalent to the kd-MG of the MG-antibody bond becoming apparently smaller. If this apparent dissociation rate constant is kd-MG', kd-MG'<kd-MG. If kd-MG and kd-anal: are approximately equal, it is presumed that the inhibition and the enhancement will occur without much difference.

Figure 7:
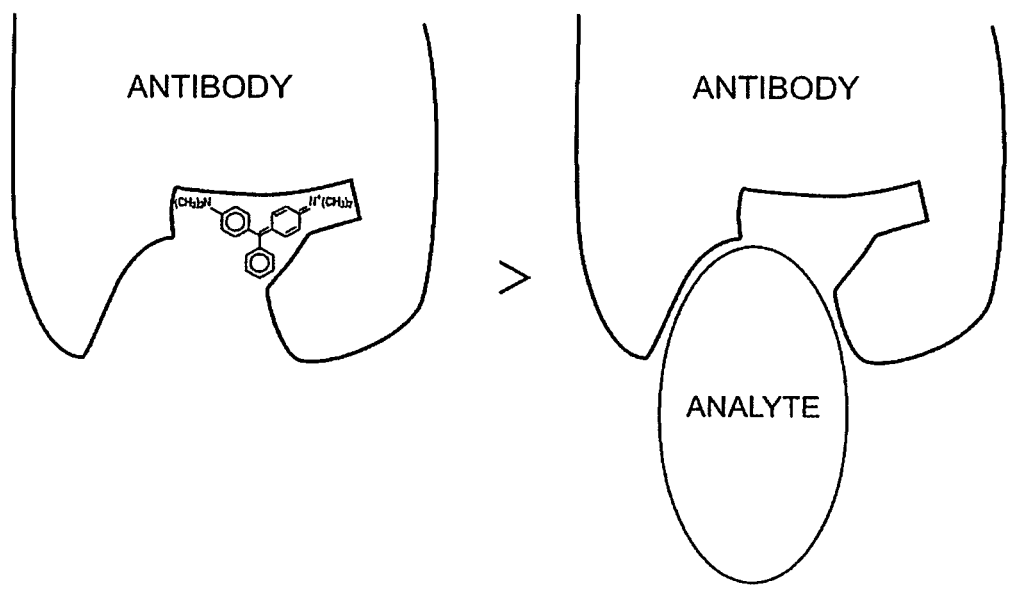
FIG. 7 is a schematic view illustrating that half-life of a MG-antibody is longer than that of an analyte-antibody.

However, if there is a difference between kd-MG and kd-anal, either the inhibition or the enhancement will become dominant. In general, the half-life $t_{1/2}$ of an antigen-antibody complex is determined as: $t_{1/2}=0.693/kd$. Therefore, the smaller the kd is, the longer the half-life is. Thus in the case where kd–MG<kd-anal, the half-life of the MG-antibody bond will become longer as shown in FIG. 7. Then even if the inhibition illustrated in FIG. 6A occurs, the analyte will dissociate from the antibody in a comparatively short time and thereafter, MG will bind and continue to form the MG-antibody bond at a longer half-life. The analyte can become bound here, and as a result, enhancement occurs (kd–MG'<kd–MG). Oppositely, if kd–anal<kd–MG (the dissociation of MG is faster), even if MG is bound, since MG becomes dissociated from the antibody prior to becoming enhanced by the binding of the analyte, enhancement will become less likely to occur and inhibition will be dominant.

Actually it is presumed that with an obtained antibody, the magnitude relationships of kd–MG and led-anal will differ from case to case, and it is presumed that either the inhibition or the enhancement will occur according to each antibody clone in the case of monoclonal antibodies and, in the case of polyclonal antibodies, according to the totality of the respective monoclonal antibodies included.

The present invention makes use of this phenomenon. If the MG-antibody bond is noted, in the case where the amounts of MG and the antibody are fixed, the degree of the inhibition or the enhancement will depend on the amount of the coexisting analyte and this will appear as a change in the fluorescence intensity of MG. Therefore, the analyte can be detected and quantified by measuring the change of the fluorescence intensity of MG.

The above-described antigen-antibody reaction concerning this invention is reversible in contrast to the prior art common knowledge that antigen-antibody reactions are irreversible. The fluorescence intensity of MG thus varies in accordance with the variation of the amount of the analyte, and the analyte can be analyzed continuously in real time by measuring this variation of fluorescence intensity.

(Preparation of a Calibration Curve)

With this invention's fluorescence analysis method, a calibration curve, which indicates the relationship between fluorescence intensity and analyte concentration, is preferably determined prior to the measurement of the real sample. A preferred embodiment of a method of preparing a calibration curve concerning this invention shall be described in detail based on a flowchart shown in FIG. 8.

Figure 8:
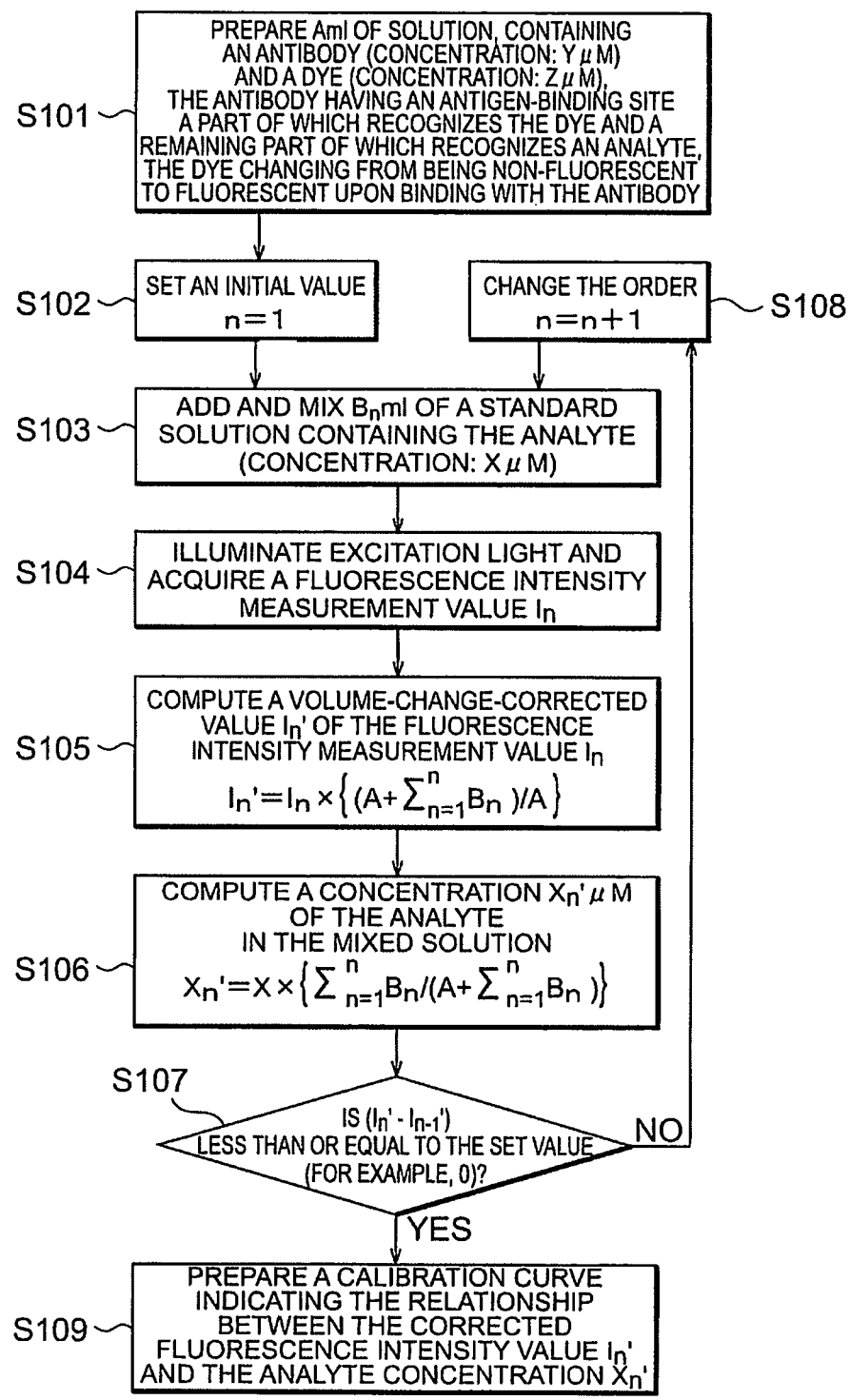
FIG. 8 is a flowchart illustrating a preferred embodiment of preparing a calibration curve concerning this invention.

With the flowchart shown in FIG. 8, first, Aml of an antibody-dye solution containing the above-described antibody and the dye at predetermined concentrations respectively (antibody concentration: YμTM, dye concentration: ZμM), the antibody having an antigen-binding site a part of which recognizes the dye and a remaining part of which recognizes an analyte, the dye changing from being non-fluorescent to fluorescent upon binding with the antibody, is prepared (S101). A solvent to be used is not restricted in particular. A buffer solution with a pH close to neutral (preferably a pH of 6.5 to 7.5) is preferable. Phosphate buffered saline can be cited as an example of the solvent.

This antibody-dye solution is then placed in a fluorescence measurement cell and set in a fluorescence spectrophotometer, with which the excitation wavelength and the fluorescence wavelength are respectively set to predetermined values in accordance with the dye to be used, etc. In this process, the initial value of the order n is set equal to 1 (S102). The temperature of the cell holder is preferably maintained at a constant temperature and the maintained temperature is preferably a temperature in the range of 25 to 37° C. The solution in the cell is preferably stirred for a predetermined amount of time.

Next, B$_n$ml of a standard solution, containing the analyte at a predetermined concentration (XμM), are added to the solution in the cell, and the mixed solution thus obtained is stirred for a predetermined amount of time to make the antigen-antibody reactions of the dye, the analyte, and the antibody proceed (S103, mixing step). The solvent used for the standard solution is not restricted in particular. A buffer solution with a pH close to neutral (for example, phosphate buffered saline) is preferable as in the case of the solvent used for the antibody-dye solution.

Next, excitation light of the predetermined excitation wavelength is illuminated on the mixed solution in the cell, and a measurement value I$_n$ is acquired by measuring the intensity of the fluorescence of the predetermined fluorescence wavelength that is emitted from the mixed solution (S104, measurement step). The specific methods of illumination of the excitation light and measurement of the fluorescent intensity are not restricted in particular. As the fluorescence intensity measurement value I$_n$, an average value or an integrated value of the fluorescence intensity within a predetermined measurement time is preferably acquired. The fluorescence intensity in the state in which the analyte is not added may be used as a blank and a value obtained by subtracting the blank value from the actual measurement value of the fluorescence intensity may be used as the measurement value I$_n$ (however, in this case, the blank value is to be subtracted after applying a correction, which is in accordance with the volume change that accompanies the addition of the standard solution, etc., to the actual measurement value).

The fluorescence intensity measurement value I$_n$, which has thus been obtained, is then corrected in accordance with the volume change accompanying the addition of the above-mentioned standard solution to compute a corrected fluorescence intensity value I$_n$', which is equivalent to the fluorescence intensity in a solution in which the antibody concentration is YμM and the dye concentration is ZμM (S105). The calculation equation for correcting the fluorescence intensity for the volume change is the following Equation (1):

$$I'_n = I_n \times \left\{ \left( A + \sum_{n=1}^{n} B_n \right) \Big/ A \right\} \quad (1)$$

and in the case where the order n=1, $$I_1' = I_1 \times \{(A+B_1)/A\} \quad (1)'$$

The analyte concentration X$_n$'μM in the mixed solution, for which the fluorescence intensity was measured, is computed (S106). The calculation equation for computing the analyte concentration in the mixed solution is the following Equation (2):

$$X'_n = X \times \left\{ \sum_{n=1}^{n} B_n \Big/ \left( A + \sum_{n=1}^{n} B_n \right) \right\} \quad (2)$$

and in the case where the order n=1, $$X_1' = X \times \{B_1/(A+B_1)\} \quad (2)'$$

After thus obtaining the corrected fluorescence value I$_n$' and the analyte concentration X$_n$' when the order n=1, 1 is added to the order n (S108). After that, as described above, addition and mixing of B$_n$ml of the standard solution (S103), acquisition of the fluorescence intensity measurement value I$_n$ (S014), computation of the corrected fluorescence value I$_n$' (S105), and computation of the analyte concentration X$_n$' (S106) are carried out again to obtain the corrected fluorescence value I$_n$' and the analyte concentration X$_n$' for the case where the order n=2. When the order n=2, the above-mentioned Equation (1) becomes:

$$I_2' = I_2 \times \{(A+B_1+B_2)/A\} \quad (1)''$$

and the above-mentioned Equation (2) becomes:

$$X_2' = X \times \{(B_1+B_2)/(A+B_1+B_2)\} \quad (2)''$$

Furthermore, until the corrected fluorescence value I$_n$' obtained in the above-described manner no longer changes even when the standard solution is added, that is, until the value of (I$_n$'−I$_{n-1}$') becomes less than or equal to a set value (for example, 0) (S107), the above-described S108→S103→S104→S105→S106→S107 are repeated (continuous measurement step) and the corrected fluorescence value I$_n$' and the analyte concentration X$_n$' for the respective cases where the order n is equal to 1 to n are obtained.

Then based on the corrected fluorescence value I$_n$' and the analyte concentration X$_n$' that have been obtained for the respective cases where the order n is equal to 1 to n, a calibration curve, indicating the relationship between the corrected fluorescence value I$_n$' and the analyte concentration X$_n$', is prepared (S109, calibration curve preparation step). The specific method of preparing the calibration curve from the numerical values is not restricted in particular. A calibration curve of higher precision can be obtained by suitable use of a known method, such as a least squares method.

(Measurement of Real Samples)

A preferred embodiment of this invention's fluorescence analysis method shall now be described in detail based on the flowchart shown in FIG. 9.

Figure 9:
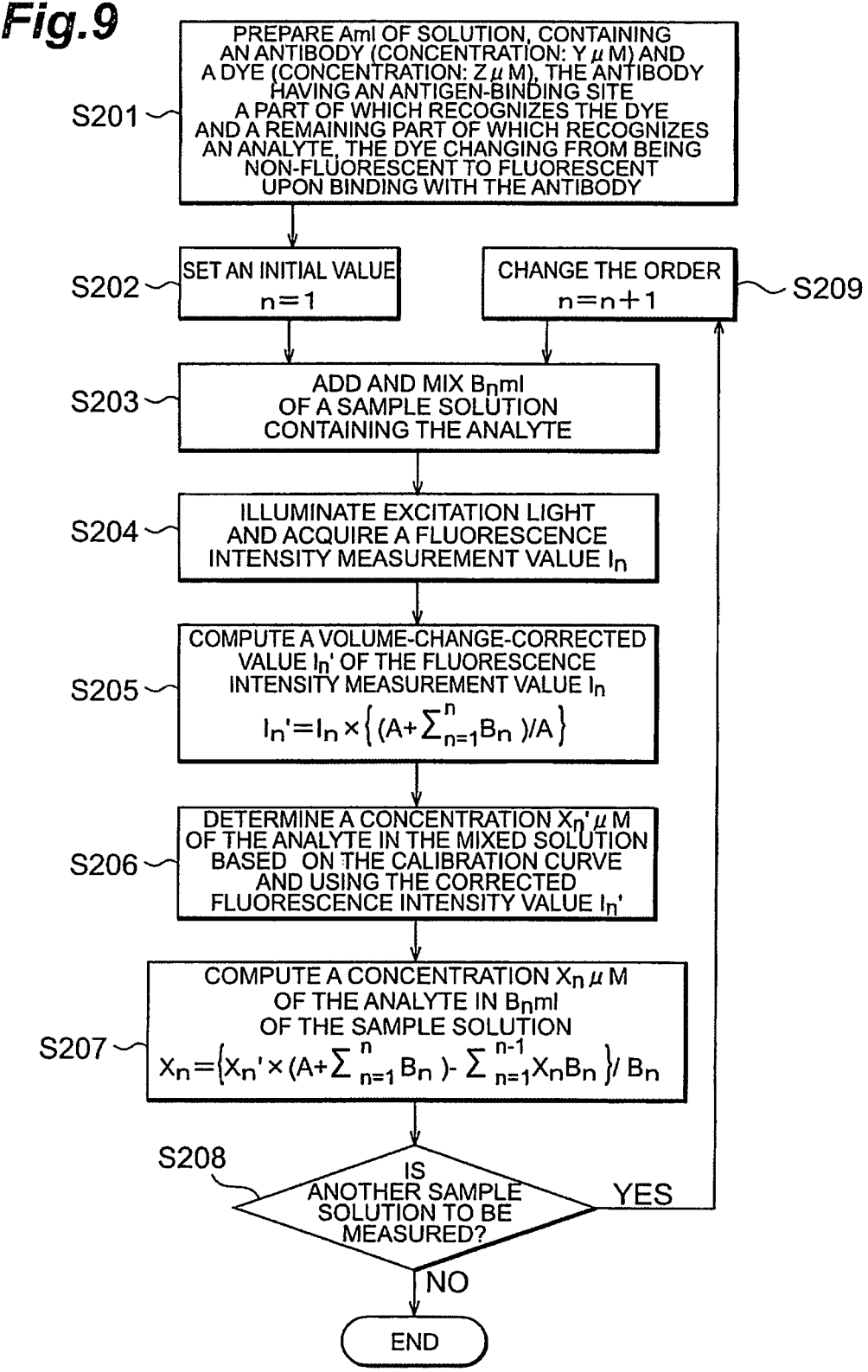
FIG. 9 is a flowchart illustrating a preferred embodiment of this invention's fluorescence analysis method.

With the flowchart shown in FIG. 9, first, as in the case of preparing the calibration curve, Aml of an antibody-dye solution containing the antibody and the dye at predetermined concentrations respectively (antibody concentration: YμM, dye concentration: ZμM), the antibody having an antigen-binding site a part of which recognizes the dye and a remaining part of which recognizes an analyte, the dye changing from being non-fluorescent to fluorescent upon binding with the antibody, is prepared (S201). A solvent to be used is not restricted in particular. A buffer solution with a pH close to neutral (for example, phosphate buffered saline) is preferable as in the case of the solvent used for preparing the calibration curve. The antibody concentration and the dye concentration in the antibody-dye solution are adjusted to be YμM and ZμM, respectively, as in the case of preparing the calibration curve.

This antibody-dye solution is then placed in a fluorescence measurement cell and set in a fluorescence spectrophotometer, with which the excitation wavelength and the fluorescence wavelength are respectively set to predetermined values as in the case of preparing the calibration curve. In this process, the initial value of the order n is set equal to 1 (S202). As in the case of preparing the calibration curve, the temperature of the cell holder is preferably maintained at a constant temperature and the maintained temperature is preferably a temperature in the range of 25 to 37° C. The solution in the cell is preferably stirred for a predetermined amount of time.

Next, $B_n$ml of a sample solution are added to the solution in the cell, and the mixed solution thus obtained is stirred for a predetermined amount of time to make the antigen-antibody reactions of the dye, the analyte, and the antibody proceed (S203, mixing step). As the sample solution, a body fluid, etc., that is to be measured may be used as it is. A solution, diluted by predetermined times with a solvent, may also be used. The solvent used for such dilution is not restricted in particular either. A buffer solution with a pH close to neutral (for example, phosphate buffered saline) is preferable as in the case of the solvent used for the antibody-dye solution.

Excitation light of the predetermined excitation wavelength is then illuminated on the mixed solution in the cell, and a measurement value $I_n$ is acquired by measuring the intensity of the fluorescence of the predetermined fluorescence wavelength that is emitted from the mixed solution (S204, measurement step). The specific methods of illumination of the excitation light and measurement of the fluorescent intensity are not restricted in particular. As in the case of preparing the calibration curve, an average value or an integrated value of the fluorescence intensity within a predetermined measurement time is preferably acquired as the fluorescence intensity measurement value $I_n$.

The fluorescence intensity measurement value $I_n$, which has thus been obtained, is then corrected in accordance with the volume change accompanying the addition of the above-mentioned sample solution to compute a corrected fluorescence intensity value $I_n'$, which is equivalent to the fluorescence intensity in a solution in which the antibody concentration is YμM and the dye concentration is ZμM (S205). The calculation equation for correcting the fluorescence intensity for the volume change is the following Equation (3):

$$I_n' = I_n \times \left\{ \left( A + \sum_{n=1}^{n} B_n \right) / A \right\} \quad (3)$$

and in the case where the order n=1, $$I_1' = I_1 \times \{(A+B_1)/A\} \quad (3)'$$

Then based on the predetermined calibration curve that indicates the relationship between the corrected fluorescence value $I_n'$ and the analyte concentration $X_n'$, the analyte concentration $X_n'$μM in the mixed solution is determined from the corrected fluorescence value $I_n'$ (S206).

The concentration $X_n$μM of the analyte in $B_n$ml of the above-mentioned sample solution can then be computed from the analyte concentration $X_n'$ in the mixed solution that has thus been determined (S207). The following Equation (4) is the calculation equation for determining the analyte concentration in the sample solution:

$$X_n = \left\{ X_n' \times \left( A + \sum_{n=1}^{n} B_n \right) - \sum_{n=1}^{n-1} X_n B_n \right\} / B_n \quad (4)$$

and when the order n=1, $$X_1 = \{X_1' \times (A+B_1)\}/B_1 \quad (4)'$$

With the present embodiment, the above-described computation of the corrected fluorescence value $I_n'$ (S205), computation of the analyte concentration $X_n'$ in the mixed solution (S206), and computation of the analyte concentration $X_n$ in the sample solution (S207) correspond to the computation step concerning this invention.

The analyte concentration $X_n$ in the sample solution can be measured as described above. Since the antigen-antibody reaction concerning this invention is reversible as described above, continuous measurement of another sample solution can also be performed as follows. If another sample solution needs to be measured (S208), the analyte concentration $X_n$ in a second (the order n=2) sample solution can be measured by adding 1 to the order n (S209), and performing again the adding and mixing of $B_n$ml of the sample solution (S203), acquisition of the fluorescence intensity measurement value $I_n$ (S204), computation of the corrected fluorescence value $I_n'$ (S205), computation of the analyte concentration $X_n'$ in the mixed solution (S206), and computation of the analyte concentration $X_n$ in the sample solution (S207). When the order n=2, Equation (3) given above becomes:

$$I_2' = I_2 \times \{(A+B_1+B_2)/A\} \quad (3)''$$

and Equation (4) given above becomes:

$$X_2 = \{X_2' \times (A+B_1+B_2) - (X_1 \times B_1)\}/B_2 \quad (4)''$$

Then until there is no longer any need to measure another sample solution (S208), the above-described S209→S203→S204→S205→S206→S207→S208 are repeated (continuous measurement step). The analyte concentrations $X_n$ in a plurality (for the order n being equal to 1 to n) of sample solutions can thus be measured in a continuous manner. Such continuous measurement of the analyte concentration can be repeated until the fluorescence intensity does not change even upon addition of sample solution due to saturation of the antibody by the analyte, etc.

With the above-described fluorescence analysis method of the present embodiment, since an antigen-antibody reaction is used, highly sensitive analysis of high selectivity is enabled by the specific molecular recognition function, and furthermore, the analyte can be measured by the fluorescence analysis selectively in a simple manner without removing foreign substances. Furthermore, since the antigen-antibody reaction concerning this invention is reversible, in contrast to the prior-art common knowledge that antigen-antibody reactions are irreversible, continuous analysis in real time is enabled by making use of the variation (the enhancement or the inhibition) of the fluorescence intensity in accordance with the variation of the amount of the analyte.

EXAMPLES

Though this invention shall now be described more specifically based on examples, this invention is not restricted to these examples, and various modifications may be made without departing from the technical idea of this invention.

Example 1

Quantification of Insulin Using an Anti-Mg-Ins Antibody Fab and MG (1-1) Reagents and Experimental Animals
The principal reagents and experimental animal used in the examples are as follows. Malachite green (MG, made by Aldrich Chemical Company, Inc.), malachite green isothiocyanate (MGITC, made by Molecular Probes Inc.), auramine O (AO, made by Aldrich Chemical Company, Inc.), dimethyl sulfoxide (DMSO, made by Wako Pure Chemical Industries Ltd.), insulin (porcine, made by Wako Pure Chemical Industries Ltd.), SDS (Sodium Dodecyl Sulfate, made by Wako Pure Chemical Industries Ltd.), anti-porcine insulin antibody (immune animal: guinea pig, made by Sigma), guinea pig (Crj; Hartley, male, 3-weeks old, SPF, weight: 225 to 240 g, provided by Charles River Japan Inc.), anesthetic (NEMB-UTAL Sodium Solution, 50 mg/ml, made by Dainabott Co., Ltd.), RAS (Ribi Adjuvant System MPL+TDM+CWS Emulsion, R-730, made by RIBI Immuno Chem Research, Inc.), 0.1M phosphate buffer (PB, pH 7.0), antigen coating buffer (50 mM sodium carbonate buffer, pH 8.4 (+) $NaN_3$), washing buffer (phosphate buffered saline, pH 7.2 (+) 0.05% Tween 20), blocking buffer (phosphate buffered saline, pH 7.2, 0.5% gelatin), 96-well microtiter plate (ELISA Testplate F-Form 2×8 F-strips bindung, made by Greiner), peroxidase-labeled goat anti-guinea pig IgG antibody (peroxidase-labeled goat anti-guinea pig IgG antibody, made by Organon Teknika Corporation Cappel Research Product), sample pretreatment cartridge (MINICENT-30 or ULTRACENT-30 for centrifugal concentration, made by Tosoli Corp., molecular weight cut-off: 30,000 daltons), color reagent kit (ABTS Peroxidase Substrate System, made by Kirkegaard & Perry Laboratories Inc.), and immobilized papain (made by Sigma).

(1-2) Equipments to be Used
The principal equipments used in the examples are as follows. Plate reader (BIO-RAD Model 3550 Microplate Reader), centrifuge (Hitachi SCR18B, made by Hitachi, Ltd.), centrifuge rotor (RPR-18-3, made by Hitachi, Ltd.), centrifuge (Labnet Force 7, made by Labnet International Inc.), centrifuge (Kokusan Model H-103RS, made by Kokusan Enshinki Co., Ltd.), vortex mixer (Automatic Mixer S-100, made by TAITEC Co., Ltd.), fluorescence spectrophotometer (Fluorolog, made by Instruments S. A. Inc.), circulator (BU150P, made by Yamato Scientific Co., Ltd.), micro stirring bar (made by Iuchi Seieido), fluorescence measurement cell (made by Iuchi Seieido), high-performance liquid chromatography (LaChrom System Interface D-7000, UV detector D-7400, pump D-7100, degasser D-7610, made by Hitachi, Ltd.)

(1-3) Experimental Methods in Common (Methods of Centrifugal Concentration of Protein Sample and Protein Quantification)
Samples containing proteins were centrifugally concentrated at 3,000×g using sample pretreatment cartridges (ULTRACENT-30 or MINISENT-30) and a centrifuge (Hitachi SCR18B or Labnet Force 7). Solvent replacement was also carried out at the same time as centrifugal concentration.

The protein concentration of each sample was quantified by the BCA method using a commercially available reagent kit (BCA Protein Assay Reagent Kit, made by PIERCE) and a standard protein solution (horse IgG standard solution, concentration: 2 mg/ml, ImmunoPure Horse IgG Standard, made by PIERCE). 25 µl each of the protein sample (diluted with PB if necessary), a dilution series (25 to 1500 µg/ml) of the standard protein solution, and PB (blank sample for a calibration curve) were placed respectively in Eppendorf tubes of 1.5 ml volume. 500 µl of a reaction solution of the reagent set (the necessary amount was prepared in accordance with the BCA Protein Assay Reagent Kit manual (made by PIERCE)) were added and stirring was performed, and then heating at 37° C. was carried out for 30 to 60 minutes. Thereafter, 300 µl from each Eppendorf tube were dispensed into a 96-well microtiter plate and the absorbance at 595 nm was measured using the plate reader. Then the protein concentration of the protein sample was determined using the calibration curve, prepared from the relationship betweeen concentration and absorbance of the standard protein solution dilution series.

(1-4) Preparation of Antigen (MG-Ins Complex)
The covalently bonded product (MG-Ins complex) of malachite green (MG) and insulin (Ins), which is to serve as the antigen, was prepared and purified as follows. 4.7 mg of insulin and 0.6 mg of malachite green isothiocyanate (MGITC) (dissolved in 20 µl of dimethyl sulfoxide) were dissolved in 2 ml of 0.1M sodium carbonate buffer (pH 9.8) and stirring at 4° C. was performed overnight upon covering the container with aluminum foil to shield light. By this reaction, the malachite green isothiocyanate becomes bonded to the amino group of insulin, thereby providing an MG-Ins complex. Then in order to eliminate unreacted components, the resulting reaction solution was placed in a gel permeation column (Econo-Pac 10DG, made by BIO-RAD), which was equilibrated with 0.1M sodium phosphate buffer (PB, pH 7.0), and eluted from the column using 4 ml of PB. An MG-Ins fraction (approximately 1.2 mg/ml) was thereby obtained.

(1-5) Preparation of Antiserum by Immunization
330 µL of the Mg-Ins fraction and 1.7 ml of physiological saline were added to a RAS vial and stirred vigorously in the vortex mixer to prepare an emulsion of the antigen and adjuvant.

Four guinea pigs were then anesthetized using the anesthetic (NEMBUTAL) (dosage: 15 ml/kg) and 0.5 ml of the above-mentioned emulsion was administered to the cervical region of each animal (by subcutaneous injection (0.1 ml×four locations) and intraperitoneal injection (0.1 ml)). After the initial immunization, the same amount of antigen was administered along with the adjuvant three times at intervals of one week for booster.

One week after the final booster, each guinea pig was etherized and laparotomized and whole blood sampling from the renal vena cava was carried out. The blood thus obtained was placed in a 10 ml test tube and a blood clot was formed by heating at 37° C. in an incubator. Thereafter, centrifugal separation (3000 rpm, 4° C., 10 min) was carried out with the centrifuge (Kokusan Model H-103RS) to separate the blood clot and obtain the antiserum.

(1-6) Measurement of the Antibody Titer

The antibody titer of the antiserum was measured using an enzyme immunoassay method. First, 6.3 ml of the antigen coating buffer was added to 700 µl of the MG-Ins fraction, 0.1 ml each of the resulting solution was dispensed in each well of a 96-well microtiter plate. The antigen (MG-Ins complex) was coated by adsorption onto the inner surfaces of the respective wells of the plate by leaving still overnight at 4° C. Thereafter, the antigen solution inside the plate was removed and the insides of the wells were washed by adding 0.1 ml of the washing buffer to the respective wells. After performing the washing operation three times, 0.1 ml of the blocking buffer was added to each well to prevent non-specific adsorption and the plate was then left still overnight at 4° C. Thereafter, the blocking buffer was removed and washing by the washing buffer was performed three times again.

Next, a dilution series (dilution ratio: 500 to 32000 times) was then prepared by diluting the antiserum with PB. A control was prepared by diluting the serum of a guinea pig, to which the antigen was not administered, by five times with PB. With respect to the antibody titer of this control, the antibody titers exhibited by the antiserum dilution series are practically equivalent to the antibody titers of 100 to 6400 times dilution. 0.1 ml each of the solutions of the antiserum dilution series and the control serum dilution was added to each well of the above-mentioned plate and antigen-antibody reactions were made to proceed by leaving still overnight at 4° C.

From the above-mentioned plate in which the antigen-antibody reactions were thus made to proceed, the antiserum dilution series and the control serum dilution were removed. Thereafter, a washing operation using 0.1 ml of the washing buffer was performed three times. 0.1 ml of a 1000 times dilution (diluted with PB) of the peroxidase-labeled goat anti-guinea pig IgG antibody was then added to each well and left still overnight at 4° C. Thereafter a washing operation using 0.1 ml of the washing buffer was performed three times. 0.1 ml of a reaction solution (prepared in accordance with the manual of the ABTS Peroxidase Substrate System reagent kit) of the color reagent (2,2'-azino-di[3-ethyl-benzthiazoline sulfonate], ABTS), which indicates the enzyme activity of peroxidase, was added to each well and the enzyme reaction was made to proceed by heating at 37° C. for 30 minutes. Thereafter, 0.1 ml of a 1% aqueous solution of SDS was added to each well to stop the enzyme reaction and the absorbance (405 nm) of each well was measured with a plate reader. The results obtained are shown in FIG. 10.

Figure 10:
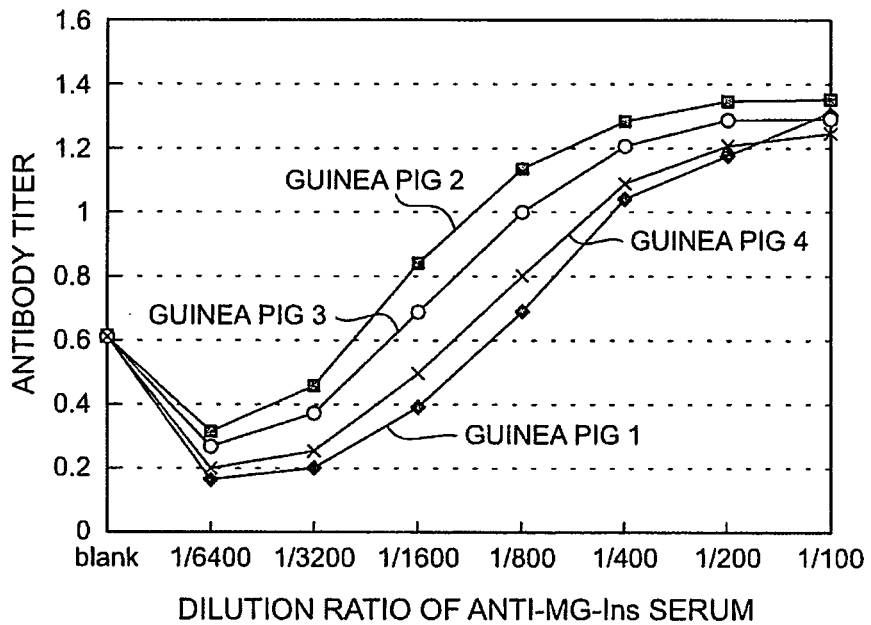
FIG. 10 is a graph showing an antibody titer of an anti-Mg-Ins serum.

As is clear from the results shown in FIG. 10, down to a dilution of 800 times or 1600 times, the antiserum of each guinea pig exhibited a higher antibody activity than the control serum, and it was thus confirmed that the antiserum specific to the MG-Ins complex was obtained. A mixture (referred to hereinafter as the "anti MG-Ins serum") of these antiserum of the four guinea pigs was then used in the following experiments.

(1-7) Preparation of an Anti-MG-Ins IgG Fraction

A plastic column (inner diameter: approx. 7 mm; length: approx. 8 cm) was filled with 0.7 ml of a resin (rprotein A Sepharaose Fast Flow (made by Pharmacia Biotech AB)), to which a protein A that binds specifically with IgG is fixed, and this column (referred to hereinafter as the "protein A column") was washed with 3 ml of PB.

1 ml of the anti-MG-Ins serum was then diluted with 1 ml of PB and filtered to remove microparticles through a cartridge type filter (0.45µ, Maishoridisk W-25-5, made by Tosoh Corp.) attached to a 5 ml disposable syringe. The filtrated solution was then added to the protein A column, and after letting the IgG bind to protein A, 10 ml of PB were run through the column to wash away components that did not bind with protein A. 4 ml of a 0.1 M citric acid buffer (pH 4.0) were then run through the protein A column to dissociate the IgG from the protein A and thereby obtain an anti-MG-Ins IgG fraction. 10 ml of PB were then run through the protein A column to regenerate the column. The anti-MG-Ins IgG fraction was then concentrated by centrifugation and, at the same time, subject to solvent replacement into PB. The above operations were repeated as necessary to prepare the necessary amount of the anti-MG-Ins IgG fraction for subsequent experiments.

(1-8) Preparation, Separation, and Purification of an Antigen-Binding Fragment (Fab) from the Anti-MG-Ins IgG Fraction A Fab was prepared by digesting IgG by the digestive enzyme, papain. First, 8.7 mg of immobilized papain were placed in an Eppendorf tube with a volume of 2.2 ml, and after adding 200 µl of PB, stirring was performed and then centrifugation was performed to remove the supernatant and wash the immobilized papain. After repeating the washing operation twice, the immobilized papain was suspended in 1 ml of a 20 mM phosphate buffer (pH 7.0, (+) 10 mM EDTA (+) 20 mM cysteine). A mixed solution of 500 µl of the 20 mM phosphate buffer and 500 µl of the anti-MG-Ins IgG fraction (IgG concentration: approx. 4.5 mg/ml) was then added to adjust the final concentration of cysteine to 10 mM. Thereafter, shaking for several hours while heating at 37° C. was carried out to make the enzyme reaction proceed. Thereafter, the enzyme reaction solution was centrifuged lightly, the supernatant was sampled, and the obtained supernatant was added to the protein A column to bind undigested IgG to protein A. Thereafter, sampling was performed by running 10 ml of PB through the protein A-column and then centrifugal concentration was carried to obtain a fraction containing the Fab of the anti-MG-Ins antibody (referred to hereinafter as the "anti-MG-Ins Fab") (5.20 mg/ml, 34.7 µM as IgG=69.3 µM as Fab).

Figure 11:
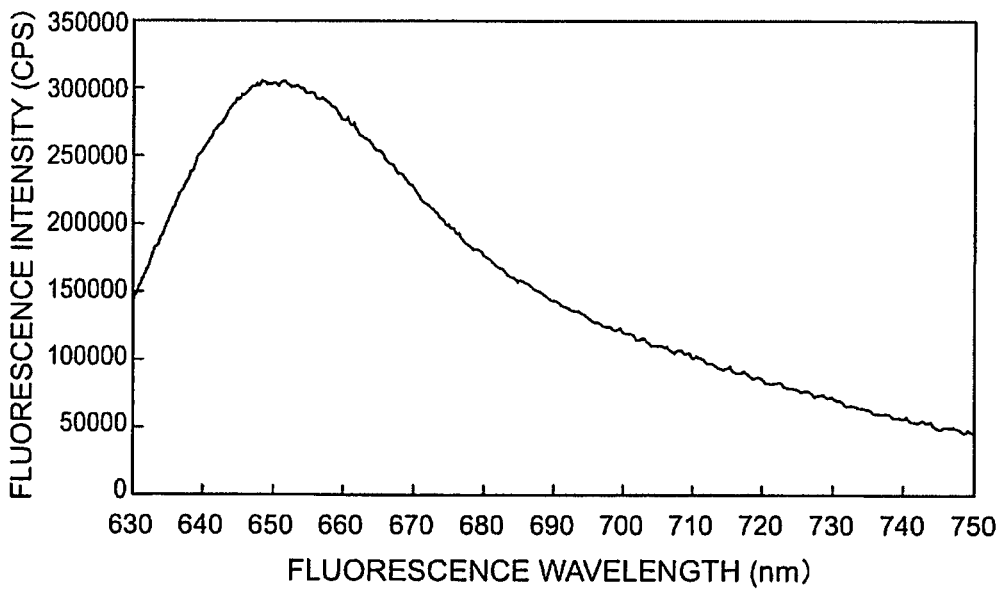
FIG. 11 is a graph showing a fluorescence spectrum of MG when an anti-MG-Ins Fab and MG are reacted.

(1-9) Measurement of the Fluorescence Spectrum of Malachite Green Bound to the Anti-MG-Ins Fab The fluorescence spectrum of MG when MG is bound to the anti-MG-Ins Fab by an antigen-antibody reaction was measured as follows. The anti-MG-Ins Fab and MG were mixed so that the respective concentrations will be 0.955 µM and 0.907 µM (using phosphate buffered saline (pH 7.2, PBS) as the solvent). Then, an antigen-antibody reaction was made to proceed by stirring for five minutes at 25° C. Then using the fluorescence spectrophotometer, the fluorescence spectrum emitted from the above-described mixed solution was measured under the conditions of an excitation wavelength of 620 nm, fluorescence wavelength of 630 to 750 nm, and bandpass width being set to 5 nm at both the excitation and fluorescence sides. FIG. 11 shows the fluorescence spectrum obtained by subtracting the phosphate buffered saline background, measured under the same conditions, from the raw data of the fluorescence spectrum that was obtained and then furthermore applying a correction according to the apparatus function. It was thus confirmed that malachite green, which was practically non-fluorescent in aqueous solution, became fluorescent upon binding with the anti-MG-Ins Fab.

Figure 12:
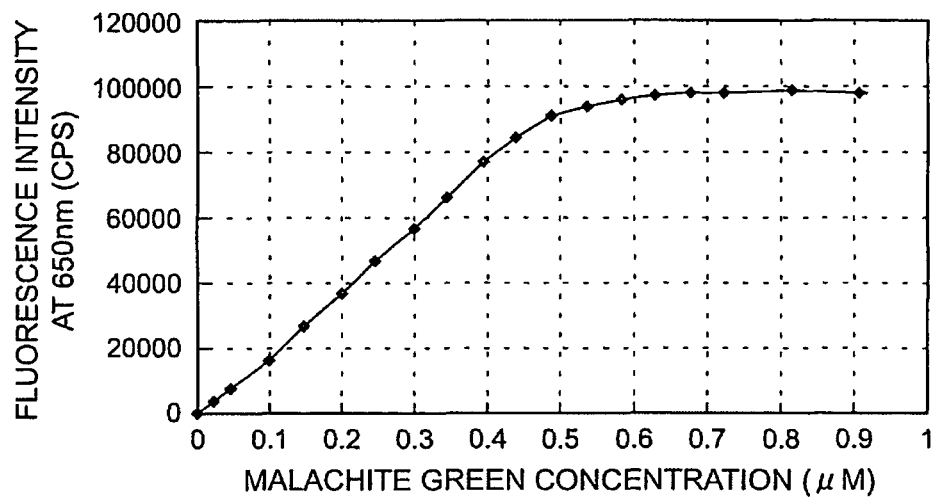
FIG. 12 is a graph showing a relationship between MG concentration and MG fluorescence intensity.

Fluorescence spectra were also measured in the same manner as the above for various MG concentrations in the range of 0 to 0.9 µM with the anti-MG-Ins Fab concentration being set at 1 µM. The results obtained are shown in FIG. 12. The ordinate axis indicates the intensity value (average value per second, CPS: counts per second) of the fluorescence emitted by MG.

Based on the results shown in FIG. 12, it was deemed that an MG concentration of 0.4 µM with respect to an anti-MG-Ins Fab concentration of 1 µM is to be employed in the subsequent quantification as a preferable relative value of the dye with respect to the antibody, that is, as a value, with which comparatively strong fluorescence of the dye can be obtained without the dye becoming saturated with respect to the antibody. This relative value may differ each time a polyclonal antibody is prepared and may also differ apparently according to the purification purity of the prepared Fab, even if the Fab is derived from the same polyclonal antibody.

(1-10) Quantification of Insulin Using the Anti-MG-Ins Fab and Malachite Green

[1-10-1] Preparation of a Calibration Curve

A calibration curve, indicating the relationship between the insulin concentration and fluorescence intensity for a fixed amount (1 µM) of the anti-MG-Ins Fab and a fixed amount (0.4 µM) of MG, was prepared as follows. Since the insulin used forms aggregate of a few molecules because of containing zinc, the insulin was dissolved in advance in PB containing SDS at a final concentration of 0.1% to dissociate the aggregate. The insulin solution thus obtained was thereafter run through a gel permeation column (Fast Desalting Column HR 10/10, made by Pharnacia), equilibrated using PBS. The insulin solution from which SDS was thus removed was used in the following quantification.

(1) The fluorescence spectrophotometer was set to an excitation wavelength of 620 nm and a fluorescence wavelength of 650 nm and the temperature of the cell holder was maintained at a fixed temperature (25° C.).

(2) 2 ml (A=2 ml) of an antibody-dye solution, containing 1 µM (Y=1 µM) of the anti-MG-Ins Fab and 0.4 µM (Z=0.4 µM) of MG, were prepared (with phosphate buffered saline (pH 7.2, PBS) as the solvent) (S101).

(3) The antibody-dye solution thus obtained was placed in a standard fluorescence measurement cell. This cell was set in the fluorescence spectrophotometer. The solution in the cell was stirred for 30 seconds with a micro stirring bar. The order was set to the initial value (n=1) (S102).

(4) 10 µl ($B_1$=0.01 ml) of the standard insulin solution (solvent is PBS) of 26.5 µM (X=26.5 µM) were then added to the solution in the cell and an antigen-antibody reaction was made to proceed by stirring for five minutes with the micro stirring bar (S103).

(5) The excitation light was illuminated onto the solution in the cell, the intensity of the fluorescence of MG that was emitted from the solution was measured for 30 seconds, and the average value per second of the fluorescence intensity (fluorescence intensity measurement value: $I_1$) was determined (S104). The fluorescence intensity when the insulin concentration is 0 µM was used as the blank, and the value obtained by subtracting the blank from the actual measurement value was used as the measurement value.

(6) The obtained fluorescence intensity measurement value ($I_1$) was then corrected (corrected in accordance with the volume change accompanying the addition of the standard solution) using the following calculation equation to determine a volume-change corrected value (corrected fluorescence intensity value: $I_1'$) (S105).

$$I_1' = I_1 \times ((A+B_1)/A) \quad (1)'$$

(7) The insulin concentration (corrected insulin concentration value: $X_1'$), in the mixed solution for which the fluorescence intensity was measured, was determined using the concentration (X) of the standard insulin solution and the following calculation equation (S106).

$$X_1' = X \times \{B_1/(A+B_1)\} \quad (2)'$$

(8) 1 was added to the order n (S108) and the above-described procedures of (4) to (7) (S103→S104→S105→S106) were repeated to determine the corrected fluorescence intensity value ($I_2'$) and the corrected insulin concentration value ($X_2'$) for the order n=2. The following calculation equations were used when the order n=2:

$$I_2' = I_2 \times \{(A+B_1+B_2)/A\} \quad (1)''$$

$$X_2' = X \times \{(B_1+B_2)/(A+B_1+B_2)\} \quad (2)''$$

(9) Until the corrected fluorescence value $I_n'$ obtained no longer changed even upon addition of the standard solution, that is, until the value of ($I_n'-I_{n-1}'$) became less than or equal to 0 (S107), the above-described procedures of (8) (S108→S103→S104→S105→S106→S107) were repeated. The corrected fluorescence value ($I_n'$) and the corrected insulin concentration value ($X_n'$) for the respective cases of the order n being equal to 1 to n were obtained. The following calculation equations were used:

$$I_n' = I_n \times \left\{ \left( A + \sum_{n=1}^{n} B_n \right) / A \right\} \quad (1)$$

$$X_n' = X \times \left\{ \sum_{n=1}^{n} B_n / \left( A + \sum_{n=1}^{n} B_n \right) \right\} \quad (2)$$

(10) The corrected fluorescence values ($I_n'$) with respect to the corrected insulin concentration values ($X_n'$) that were obtained for the respective cases of the order n being equal to 1 to n were plotted on a graph to prepare a calibration curve for an insulin concentration of 0 to 1.8 µM (S109). The calibration curve thus obtained is shown in FIG. 13.

Figure 13:
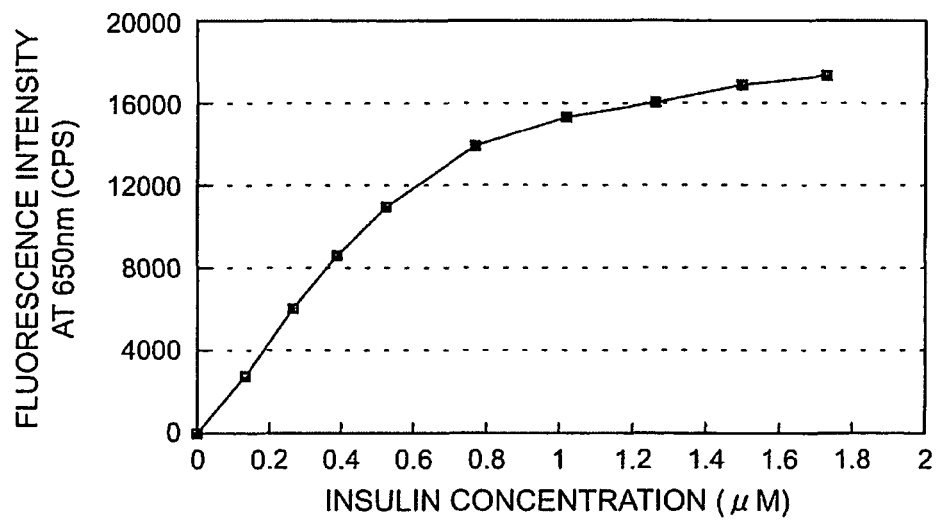
FIG. 13 is a graph showing a relationship (a calibration curve) between insulin concentration and MG fluorescence intensity.

From the results shown in FIG. 13, it was confirmed that when the anti-MG-Ins Fab and malachite green are used, the fluorescence intensity of malachite green increases, that is, enhancement of fluorescence occurs accompanied by the increase of the insulin concentration. It was also confirmed that since there is a positive correlation between the corrected insulin concentration value ($X_n'$) and the corrected fluorescence intensity value ($I_n'$) in the range of 0 to 1.7 µM, an insulin concentration in this range can be quantified by measuring the fluorescence intensity of malachite green. It was also confirmed that quantification of insulin concentration is possible even for a low concentration of approximately 0.13 µM and that the detection sensitivity (approx. 0.1 µM) is thus high.

[1-10-2] Measurement of Real Samples

Using the calibration curve obtained as described above, the quantification of the insulin concentration in real samples was carried out as follows. The sample solution of an real sample was a body fluid, a concentrate of the body fluid, or a body fluid diluted with PBS, etc.

(11) The fluorescence spectrophotometer was set to an excitation wavelength of 620 nm and a fluorescence wavelength of 650 nm and the temperature of the cell holder was maintained at a fixed temperature (25° C.).

(12) 2 ml (A=2 ml) of an antibody-dye solution, containing 1 µM (Y=1 µM) of the anti-MG-Ins Fab and 0.4 µM (Z=0.4 µM) of MG, were prepared (using phosphate buffered saline (pH 7.2, PBS) as the solvent) (S201).

(13) The antibody-dye solution thus obtained was placed in a standard fluorescence measurement cell. The cell was set in the fluorescence spectrophotometer, and the solution in the cell was stirred for 30 seconds with a micro stirring bar. The order was set to the initial value (n=1) (S202).
(14) 20 μl ($B_1$=2.020 ml) of a sample solution were then added to the solution in the cell and an antigen-antibody reaction was made to proceed by stirring for five minutes with the micro stirring bar (S203).
(15) The excitation light was illuminated onto the solution in the cell, the intensity of the fluorescence of MG that was emitted from the solution was measured for 30 seconds. The average value per second of the fluorescence intensity (fluorescence intensity measurement value: $I_1$) was determined (S204). The fluorescence intensity when the sample solution was not added was used as the blank, and the value obtained by subtracting the blank from the actual measurement value was used as the measurement value.
(16) The obtained fluorescence intensity measurement value ($I_1$) was then corrected (corrected in accordance with the volume change accompanying the addition of the sample solution) using the following calculation equation to determine a volume-change-corrected value (corrected fluorescence intensity value: $I_1'$) (S205).

$$I_1' = I_1 \times \{(A+B_1)/A\} \quad (3)'$$

(17) The insulin concentration ($X_1'$) in the mixed solution was determined from the above-mentioned fluorescence intensity value ($I_1'$) based on the predetermined calibration curve that indicates the relationship between the corrected fluorescence value ($I_n'$) and the corrected insulin concentration value ($X_n'$) (S206).
(18) The insulin concentration ($X_1$) in the sample solution was then determined using the obtained insulin concentration ($X_1'$) in the mixed solution and the following calculation equation (S207):

$$X_1 = \{X_1' \times (A+B_1)\}/B_1 \quad (4)'$$

The insulin concentration ($X_1$) in the sample solution that was thus determined was 0.26 μM and was confirmed to agree with the insulin concentration in the sample solution that was determined by another method (BCA method).
(19) If there was a need to measure another sample solution subsequently (S208), 1 was added to the order n (S209) and the above-described procedures of (14) to (18) (S203→S204→S205→S206→S207) were repeated to determine the insulin concentration ($X_2$) in the other sample solution. The following calculation equations were used for the order n=2:

$$I_2' = I_2 \times \{(A+B_1+B_2)/A\} \quad (3)''$$

$$X_2 = \{X_2' \times (A+B_1+B_2) - (X_1 \times B_1)\}/B_2 \quad (4)''$$

(20) Until there was no longer a need to measure yet another sample solution (S208), the insulin concentrations ($X_n$) of a plurality (for the order n being equal to 1 to n) could be measured continuously by repeating the above-described procedures of S209→S203→S204→S205→S206→S207→S208. Such continuous measurements could be repeated until the fluorescence intensity no longer changed even upon addition of sample solution due to saturation of the antibody by insulin, etc. The following calculation equations were used:

$$I_n' = I_n \times \left\{ \left(A + \sum_{n=1}^{n} B_n\right) \Big/ A \right\} \quad (3)$$

$$X_n = \left\{ X_n' \times \left(A + \sum_{n=1}^{n} B_n\right) - \sum_{n=1}^{n-1} X_n B_n \right\} \Big/ B_n \quad (4)$$

Example 2

[Quantification of Insulin Using an Fab of an Anti-MG-Ins Antibody and AO]

With auramine O (AO), which is practically non-fluorescent in an aqueous solution, a part of the chemical structure is in common to the chemical structure of malachite green. The present inventor thus assumed that AO will also cross-react with anti-MG-Ins IgG and anti-MG-Ins Fab to change to being fluorescent. Since AO is smaller in molecular size in comparison to MG, the present inventor assumed that AO is weak in binding with an antibody and high in kd. There is thus the possibility that the kd of AO is greater than the kd of insulin, and in this case, the present inventor assumed that, unlike the case of Example 1, the existence of insulin will cause inhibition of fluorescence and that a negative correlation will exist between the insulin concentration and the fluorescence intensity. The following experiments were thus performed using AO in place of MG to quantify insulin based on such a negative correlation between the insulin concentration and the fluorescence intensity.

Figure 14:
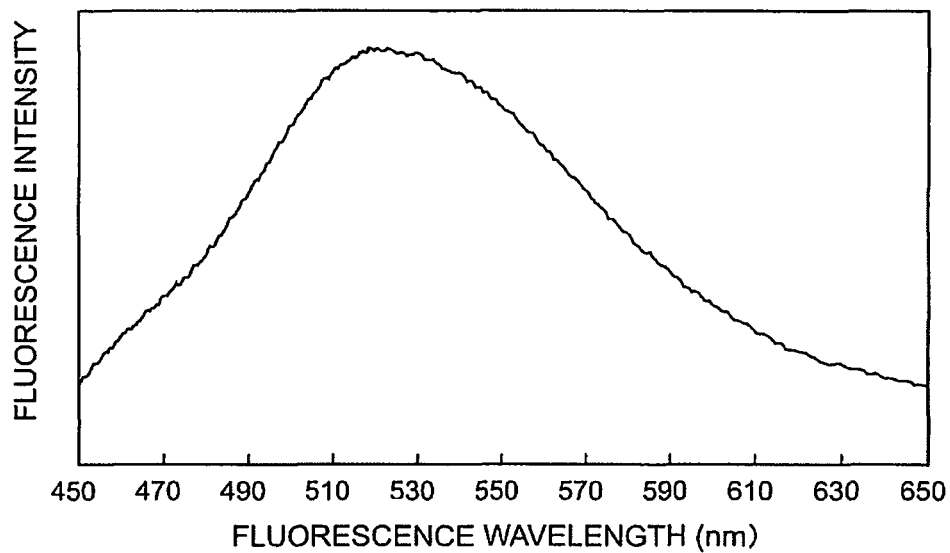
FIG. 14 is a graph showing a fluorescence spectrum of AO when an anti-MG-Ins IgG and AO are reacted.

(2-1) Measurement of the Fluorescence Spectrum of Auramine O Bound to the Anti-MG-Ins IgG The fluorescence spectrum of AO when AO is bound to the anti-MG-Ins IgG by an antigen-antibody reaction was measured as follows. The anti-MG-Ins IgG and AO were mixed so that the respective concentrations will be 1 μM and 1 μM (using phosphate buffered saline (pH 7.2, PBS) as the solvent). An antigen-antibody reaction was made to proceed by stirring for five minutes at 25° C. Then using the fluorescence spectrophotometer, the fluorescence spectrum emitted from the above-described mixed solution was measured under the conditions of an excitation wavelength of 400 nm, fluorescence wavelength of 450 to 650 nm, and bandpass width being set to 5 nm at both the excitation and fluorescence sides. FIG. 14 shows the fluorescence spectrum which is obtained by subtracting the phosphate buffered saline background, measured under the same conditions, from the raw data of the fluorescence spectrum that was obtained and then furthermore applying a correction according to the apparatus function. It was thus confirmed that auramine O, which was practically non-fluorescent in aqueous solution, also became fluorescent upon binding with the anti-MG-Ins IgG.

(2-2) Quantification of Insulin Using Auramine O and the Anti-MG-Ins Fab

Preparation of a Calibration Curve

A calibration curve was prepared for insulin concentrations in the range of 0 to 7.7 μM in the same manner as described above in [1-10-1] other than the changes of setting the anti-MG-Ins Fab concentration to 2 μM, using 0.4 μM of auramine O in place of 0.4 μM of malachite green, setting the excitation wavelength to 400 nm, and setting the fluorescence wavelength to 520 nm. The calibration curve that was obtained is shown in FIG. 15.

Figure 15:
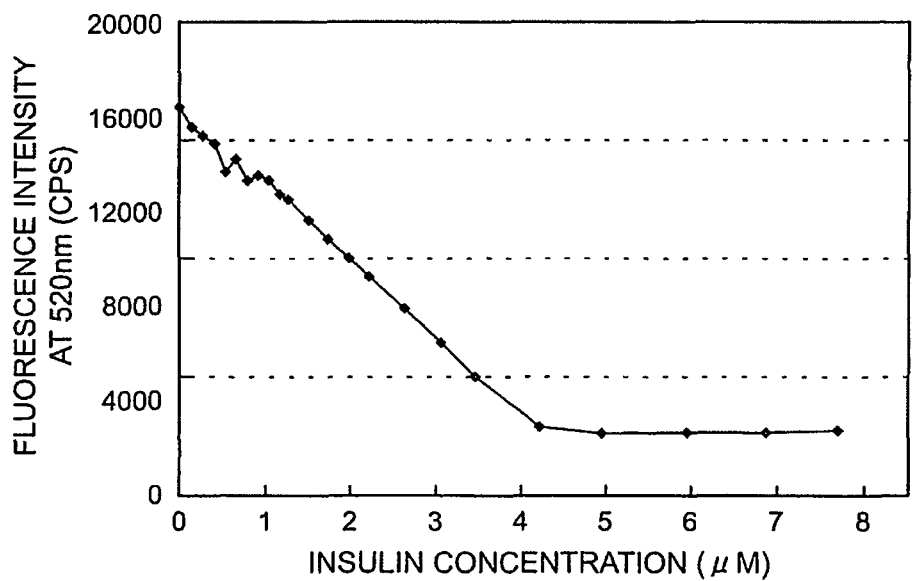
FIG. 15 is a graph showing a relationship (a calibration curve) between insulin concentration and AO fluorescence intensity.

From the results shown in FIG. 15, it was confirmed that when the anti-MG-Ins Fab and auramine O are used, the fluorescence intensity of auramine O decreases with an increase in insulin concentration, that is, inhibition of fluorescence occurs. It was also confirmed that, since there is a negative linear correlation between the corrected insulin concentration value ($X_n'$) and the corrected fluorescence intensity value ($I_n'$) in the range of 0 to 4.23 µM, an insulin concentration in this range can be quantified by measuring the fluorescence intensity of auramine O. It was also confirmed that quantification of insulin concentration is possible even for a low concentration of approximately 0.13 µM and that the detection sensitivity (approx. 0.1 µM) is high. As for the reason why the AO fluorescence intensity reached a fixed value in the region of insulin concentrations higher than 4.23 µM, the present inventor assumed that since the anti-MG-Ins IgG, from which the anti-MG-Ins Fab originated, is a polyclonal antibody, anti-MG-Ins IgG contained an IgG that becomes bonded to AO extremely strongly.

[2-2-2] Measurement of Real Samples

The insulin concentration ($X_1$) in a sample solution was determined in the same manner as described above in [1-10-2] using the calibration curve obtained as described above and other than the changes of setting the anti-MG-Ins Fab concentration to 2 µM, using 0.4 µM of auramine O in place of 0.4 µM of malachite green, setting the excitation wavelength to 400 nm, and setting the fluorescence wavelength to 520 nm. The insulin concentration ($X_1$) in the sample solution that was thus determined was 0.26 µM and was confirmed to agree with the insulin concentration in the sample solution that was determined by another method (BCA method).

By repeating, in the same manner as described above in [1-10-2] other than the above-mentioned changes, the above-described procedures of S209→S203→S204→S205→S206→S207→S208 until there was no longer a need to measure yet another sample solution, the insulin concentrations ($X_n$) of a plurality (for the order n being equal to 1 to n) could be measured continuously. Such continuous measurements could be repeated until the fluorescence intensity no longer changed even upon addition of sample solution due to saturation of the antibody by insulin, etc.

Figure 16:
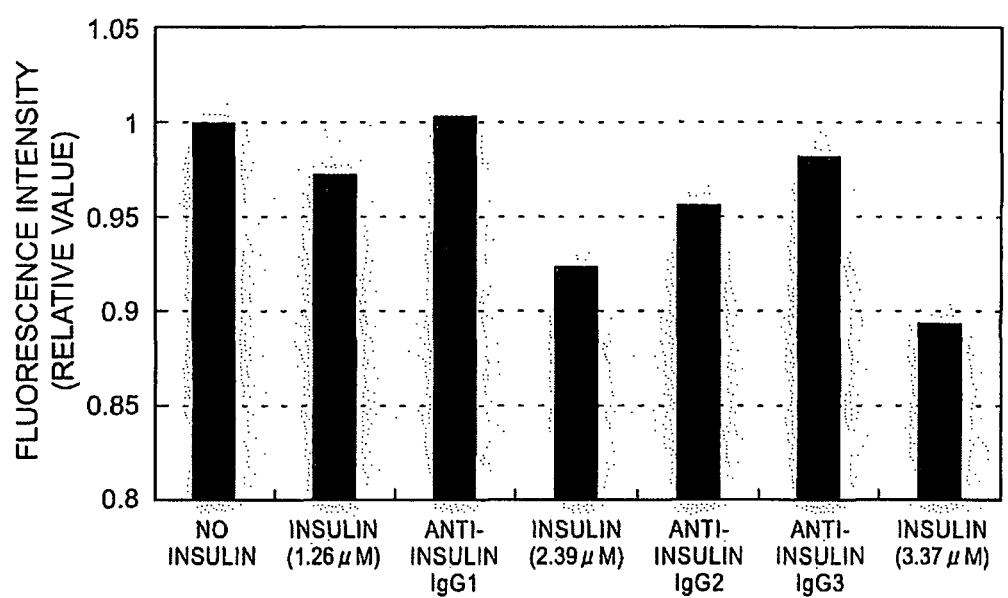
FIG. 16 is a graph showing a variation of AO fluorescence intensity when insulin and anti-insulin IgG are added repeatedly.

(2-3) Verification test concerning the reversibility of the antigen-antibody reactions The following experiment was carried out in order to confirm that, when the free insulin concentration in the same sample is varied by repeating the addition of insulin and the addition of anti-porcine insulin IgG (referred to hereinafter as "anti-insulin IgG") in a solution containing the anti-MG-Ins Fab and auramine O, the measurement values of this invention vary following the variation of the free insulin concentration, that is, the antigen-antibody reactions concerning this invention are reversible and enable analysis in real time. The measurement of fluorescence intensity was carried out under the same measurement conditions as described above in [2-2-1]. The obtained results are shown in FIG. 16.

First, 2 ml of a PBS solution, containing 2 µM of the anti-MG-Ins Fab and 0.4 µM of auramine O, were prepared. The AO fluorescence intensity was measured upon placing the solution in a cell. The florescence intensity at this time was set to a relative value of 1.

Insulin was then added to the solution in the cell so that the insulin concentration will be 1.26 µM. When the fluorescence intensity was measured after five minutes of stirring, the relative value of the AO fluorescence intensity was found to have dropped to approximately 0.97.

A fixed amount (0.135 µM) of the anti-insulin IgG was then added to this solution. When the fluorescence intensity was measured after stirring in the same manner, the relative value of the AO fluorescence intensity was found to have returned substantially to approximately 1. The AO fluorescence intensity returned to the original value since the anti-insulin IgG and insulin became bonded and free insulin no longer existed in the solution.

When insulin was then added again to this solution so that the insulin concentration will be 2.39 µM. When the fluorescence intensity was measured after stirring in the same manner, the relative value of the AO fluorescence intensity was found to have decreased again. However, when the anti-insulin IgG was added furthermore to this solution in twice (first time: 0.128 µM, second time: 0.127 µM), the relative value of the AO fluorescence intensity was found to have recovered. Then insulin was added again to this solution so that the insulin concentration will be 3.37 µM, when the fluorescence intensity was measured after stirring in the same manner, the relative value of the AO fluorescence intensity was found to have decreased.

From the results shown in FIG. 16, it was confirmed that the antigen-antibody reactions concerning this invention are reversible and that the measurement value (fluorescence intensity) by this invention's method reversibly follows the variation (increase or decrease) of the amount of the analyte. It was also confirmed that, the analyte can be measured in real time by measuring the variation of the fluorescence intensity since the measurement value (fluorescence intensity) by this invention's method is correlated with the amount of analyte.

By this invention, a fluorescence analysis method can be provided that enables analysis (including imaging) of in vivo substances, etc., using antigen-antibody reactions to be carried out simply, at high sensitivity, and yet continuously and in real time.

What is claimed is:

1. A fluorescence analysis method comprising:
   (a) mixing a sample solution comprising an analyte in free form with an antibody-dye solution comprising an antibody and a dye in free form at predetermined concentrations to form a mixed solution;
   (b) measuring an intensity of fluorescence emitted from the mixed solution to obtain a measurement value; and
   (c) determining a concentration of the analyte in the mixed solution from the measurement value by comparing the measurement value to a calibration curve,
   wherein the antibody is capable of binding both the free forms of the analyte and the dye;
   and wherein the antibody is capable of binding simultaneously to both the free forms of the analyte and the dye in a same binding site on the antibody, a part of which binds to the dye and a remaining part of which binds to the analyte,
   wherein the amount of dye bound to the antibody is influenced by the concentration of the analyte in the mixed solution,
   wherein fluorescence intensity of the dye changes when the antibody is bound, and the intramolecular motion of the dye is restrained, and
   wherein an antigen used to prepare the antibody comprises the analyte covalently bound to the dye.

2. The fluorescence analysis method of claim 1, further comprising:
   (d) adding and mixing more sample solution into the mixed solution and then repeating said measuring and determining to repeatedly determine analyte concentrations.

3. The fluorescence analysis method of claim 2,
   wherein said determining comprises:
   obtaining a corrected fluorescence intensity value by correcting the measurement value in accordance with volume change that accompanies an addition of the sample solution;

determining the analyte concentration in the mixed solution from the corrected fluorescence intensity value based on a predetermined relationship between corrected fluorescence intensity values and analyte concentration in the mixed solution; and determining the analyte concentration in the sample solution from the analyte concentration in the mixed solution.

4. The fluorescence analysis method of claim 1, wherein said determining comprises:

obtaining a corrected fluorescence intensity value by correcting the measurement value in accordance with volume change that accompanies an addition of the sample solution;

determining the analyte concentration in the mixed solution from the corrected fluorescence intensity value based on a predetermined relationship between corrected fluorescence intensity values and analyte concentration in the mixed solution; and determining the analyte concentration in the sample solution from the analyte concentration in the mixed solution.

5. The fluorescence analysis method of claim 1, wherein preparing the calibration curve comprises:

obtaining a corrected fluorescence intensity value by correcting the measurement value in accordance with volume change that accompanies an addition of the standard solution;

computing the analyte concentration in the mixed standard solution; and determining a relationship between the corrected fluorescence intensity value and the analyte concentration in the mixed standard solution.

6. The fluorescence analysis method of claim 1, wherein the antigen comprises the analyte covalently bound to malachite green.

7. The fluorescence analysis method of claim 1, wherein the antibody is an antigen-binding fragment prepared from an IgG fraction obtained by purification from an antiserum.

8. The fluorescence analysis method of claim 1, wherein the analyte is selected from the group consisting of proteins, hormones, vitamins, environmental pollutants, and medical drugs that are to be subject to immunoassay.

9. The method of claim 1, wherein the calibration curve is obtained by (a) mixing a standard solution and an antibody-dye solution, the standard solution comprising the analyte at a predetermined concentration, the antibody-dye solution comprising the antibody and the dye at predetermined concentrations to form a mixed standard solution, (b) measuring an intensity of fluorescence emitted from the mixed standard solution to obtain a measurement value; and (c) adding and mixing more standard solution into the mixed standard solution and thereafter repeating said measuring to obtain the calibration curve.

10. The fluorescence analysis method of any one of claims 2, 4, 3, 1, and 9, wherein the dye is a dye selected from the group consisting of dyes having a triphenylmethane structure and dyes having a diphenylmethane structure.

11. The fluorescence analysis method of claim 10, wherein the dye is malachite green.

* * * * *